United States Patent [19]
Mazess et al.

[11] Patent Number: 5,841,833
[45] Date of Patent: Nov. 24, 1998

[54] DUAL-ENERGY X-RAY DETECTOR PROVIDING SPATIAL AND TEMPORAL INTERPOLATION

[75] Inventors: Richard B. Mazess; David M. Gauntt, both of Madison, Wis.

[73] Assignee: Lunar Corporation, Madison, Wis.

[21] Appl. No.: 814,368

[22] Filed: Mar. 11, 1997

Related U.S. Application Data

[63] Continuation-in-part of Ser. No. 73,264, Jun. 7, 1993, Pat. No. 5,306,306, and Ser. No. 551,685, Nov. 1, 1995, abandoned, which is a continuation-in-part of Ser. No. 241,270, May 10, 1994, Pat. No. 5,509,042, which is a continuation-in-part of Ser. No. 67,651, May 26, 1993, Pat. No. 5,291,537, which is a division of Ser. No. 944,626, Sep. 14, 1992, Pat. No. 5,228,068, said Ser. No. 73,264, is a continuation of Ser. No. 862,096, Apr. 2, 1992, abandoned, which is a continuation of Ser. No. 655,011, Feb. 13, 1991, abandoned.

[51] Int. Cl.$^6$ ...................................................... H05G 1/64
[52] U.S. Cl. ...................... 378/98.9; 378/98.8; 378/146; 250/367; 250/370.09
[58] Field of Search ................................ 378/56, 54, 55, 378/57, 62, 98.9, 98.8, 98.11, 98.12, 146; 256/370.06, 370.09, 370.08, 363.01, 367

[56] References Cited

U.S. PATENT DOCUMENTS

| | | | |
|---|---|---|---|
| 3,267,283 | 8/1966 | Kapany | 378/98.9 |
| 5,319,547 | 6/1994 | Krug et al. | 382/22 |
| 5,418,832 | 5/1995 | Barnes | 378/146 |
| 5,436,453 | 7/1995 | Chang et al. | 250/370.06 X |

*Primary Examiner*—David P. Porta
*Attorney, Agent, or Firm*—Quarles & Brady

[57] ABSTRACT

A side-by-side x-ray detector provides dual energy measurements in a scanned configuration where high and low energy detector elements are interspersed. Alternating high and low energy detector elements in both row and column allows for interpolation and time and space providing virtual measurements at identical times and locations reducing image artifacts and errors caused by edges in the image. The resulting detector may be suitable for a variety of imaging applications including medical densitometry and baggage scanning.

16 Claims, 18 Drawing Sheets

FIG. II

DUAL-ENERGY X-RAY DETECTOR PROVIDING SPATIAL AND TEMPORAL INTERPOLATION

CROSS-REFERENCE TO RELATED APPLICATIONS

This is a continuation-in-part of application Ser. No. 08/551,685 filed Nov. 1, 1995, now abandoned, which is a continuation-in-part of application Ser. No. 08/241,270 filed May 10, 1994, now U.S. Pat. No. 5,509,042, based on a PCT filing, PCT/US93/08515, of Sep. 10, 1993 which is a continuation-in-part of Ser. No. 08/067,651 filed May 26, 1993, now U.S. Pat. No. 5,291,537, which is a divisional of Ser. No. 944,626, now U.S. Pat. No. 5,228,068 filed Sep. 14, 1992; and a continuation-in-part of application Ser. No. 08/073,264 filed Jun. 7, 1993, now U.S. Pat. No. 5,306,306, which is a continuation of application Ser. No. 07/862,096 filed Apr. 2, 1992, now abandoned, which is a continuation of application Ser. No. 07/655,011 filed Feb. 13, 1991, now abandoned.

BACKGROUND OF THE INVENTION

The present invention relates to dual energy detectors that may find use in x-ray imaging equipment producing images which distinguish between multiple basis materials. Such systems find use in medical systems, for example, bone densitometers, and in industrial inspection systems such as airport baggage scanners.

The measurement of x-ray energy attenuated by an imaged object in two distinct energy bands can be used to determine information about the material out of which the imaged object is composed. Generally attenuation is a function of x-ray energy according to two attenuation mechanisms of photoelectric absorption and Compton scattering. These two mechanisms differ among materials of different atomic numbers. For this reason, measurements at two energies can be used to distinguish between two different basis materials.

Dual energy x-ray techniques can be used to separate bony tissue from soft tissue in medical imaging, for example, or to identify hazardous materials, for example, in baggage scanning.

In a switched mode system dual energy x-ray system, the voltage on the x-ray tube is periodically changed from a high to low voltage shifting the energy spectrum of the produced x-ray beam. A single set of solid state detectors illuminated by the beam collects measurements of the imaged object at the different energy outputs. Here x-ray detectors having broad-band sensitivity to different energies are used. A so-called K-edge filter may be placed in the beam before the x-ray detector to sharpen the output spectrum of the x-rays at the different energies.

In an alternative approach, a broad band x-ray beam may be produced having multiple energies, and the discrimination between x-ray energies may be done by the detector which provides separate output signals for received high and low x-ray energies. One type of detector used in this approach is a stacked array detector in which two detector elements are stacked on top of each other. Typically, a front most detector will measure total x-ray flux and a rearward detector will measure only higher energy x-ray photons not stopped by an intervening filter. Low energy photons may be deduced from these two measurements.

An alternative side-by-side detector construction described in the predecessor applications to this application, two rows of detector elements are placed side-by-side and scanned along the imaged object in a direction perpendicular to the rows. The detector elements of the first row has a different energy sensitivity from that of the second row. Scanning the imaged object causes the two rows to pass over the same areas of the imaged object, each making measurements. High and low energy measurements for a given location in the imaged object are made at slightly different times.

While this detector construction has a number of advantages, the fact that the high and low energy readings are made at different times may produce minor image artifacts if the patient moves between the measurements, even though the time between measurements is slight. Movements may include involuntary muscle movement in the case of a patient and/or vibrations of elastic elements in case of non-living objects.

Interpolation between multiple high or low energy measurements taken at different times to produce a virtual measurement of the high and low energies at a single, common time and single, common location is not possible with this detector design. This is because any two measurements, of either high or low energy that might be used for interpolation to a common time and common location, are displaced from that time and location by different amounts preventing the use of a common interpolation factor. In short, the architecture of the detector prevents interpolation from being used to eliminate motion artifacts.

BRIEF SUMMARY OF THE INVENTION

The present invention provides a new architecture for side-by-side, dual energy detectors used in a scanning application. Individual high and low energy detector elements are arranged within the rows of the detector in alternating fashion so that measurements taken with either detector type (high or low energy) can be interpolated to a common time and location to measurements taken with the other detector type. In one case, the configuration requires interpolation in either time or space, but not both. In a second configuration, interpolation in both time and space is required but a single interpolation factor may be used for each measurement.

In the preferred embodiment, high and low energy detector elements are alternated in each row and in each column so that high and low energy detector elements touch other similar detector elements only at corners.

Specifically, the present invention provides a dual energy detector having first low energy detector elements detecting incident low energy photons, each over a predetermined detector area, and high energy detector elements detecting incident high energy photons each over a predetermined area, wherein the high and low energy detector elements are arranged in at least one row of alternating high and low energy detector elements. The detector may include a scanning assembly moving the detector perpendicularly to the rows. The columns may also be arranged so that high and low energy detectors elements are alternated.

It is one object of the invention to provide the benefits of a side-by-side radiation detector with reduced possibility motion artifacts and of edge artifacts. Edge artifacts are those caused by spatial interpolation where the imaged material changes abruptly causing a spatial interpolation to be inaccurate.

Motion artifacts are reduced by allowing interpolation to a common time of measurements taken at different spatial locations. This interpolation is permitted by the above staggering of high and low energy detector elements.

Edge artifacts are reduced by the staggered column design which allows three point interpolation and which ensures at least one detector type of the interpolation has exactly the same location as its complement detector type.

DETAILED DESCRIPTION OF THE INVENTION

Description of the Preferred Embodiment

Densitometry Hardware

Figure 1:
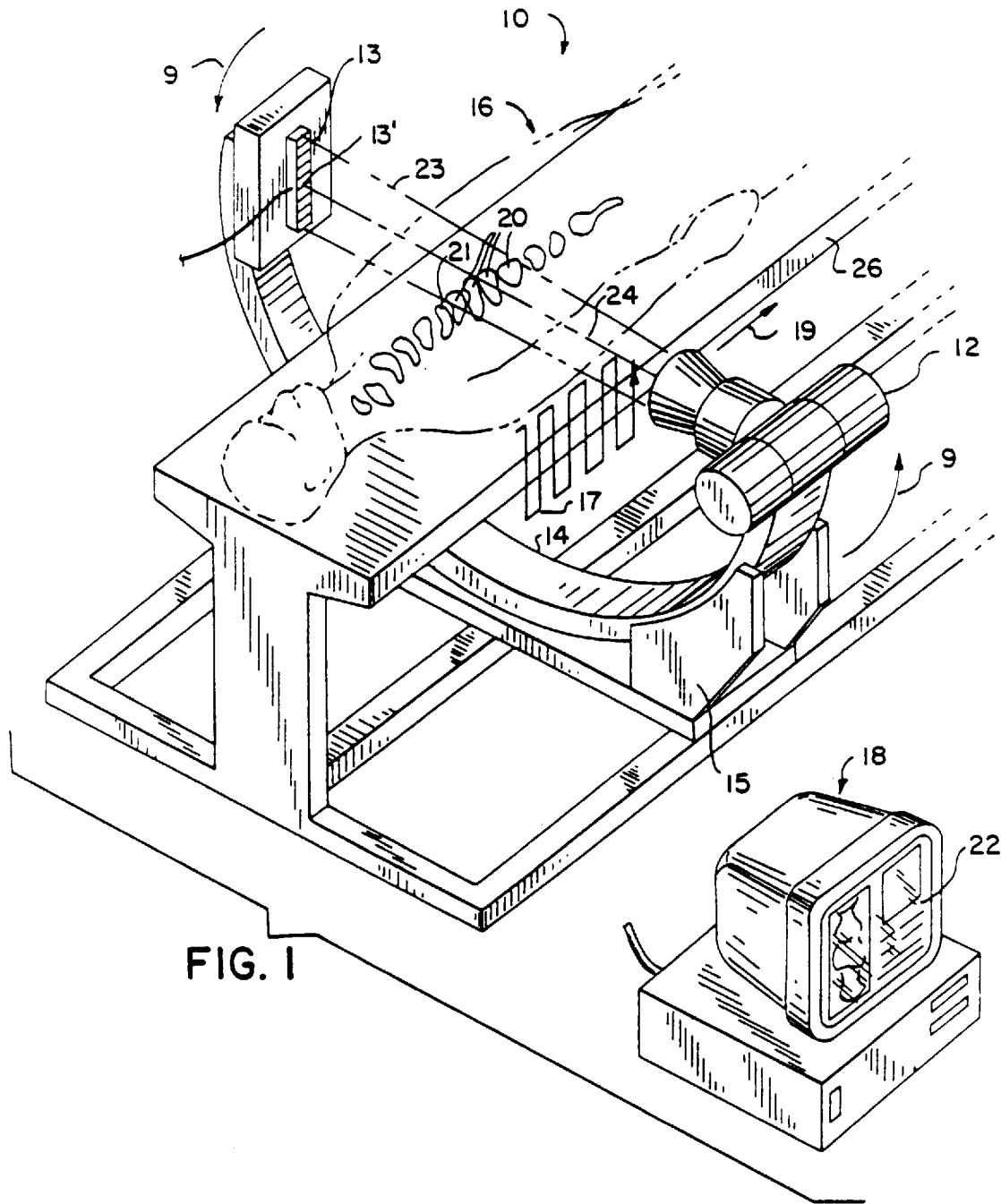
FIG. 1 is a schematic illustration of an instrument for use in the present invention showing a first embodiment employing a pencil beam and a raster scan and a second embodiment employing a fan beam and a linear scan.

Shown in FIG. 1 is a simplified schematic of an x-ray based digital x-ray device 10 of the type described in the preferred embodiment of the present invention. The digital x-ray device 10 includes a dual energy x-ray radiation source 12 and a detector 13, both of which are mounted on a rotatable C-arm 14, which extends on either side of a supine patient 16 so as to direct and receive radiation along a radiation axis 24 through the patient 16. The C-arm 14 is designed to be rotated in a vertical plane as indicated by arrows 9 as supported by a collar 15 so as to allow both an anterior-posterior ("AP") view of the spine or other bones or a lateral view of the same. The C-arm 14 may also be moved longitudinally along the patient's body in a scanning direction 19 and may be positioned under the control of servo motors as is understood in the art.

The digital x-ray device 10 of the preferred embodiment has the capability of switching from a dual energy x-ray to a single energy x-ray mode. "Single-energy x-ray" refers to ionizing radiation at a narrow band of energies of a few keV in the diagnostic imaging range (20–100 keV). "Dual energy x-ray" or "polychromatic x-ray" refers to radiation at two or more bands of energy emitted simultaneously or in rapid succession, or a single broad band energy of more than a few keV over the diagnostic imaging range.

Switching from dual energy to single energy may be done either by affecting the source, e.g., removing or adding a K-edge filter, or by controlling the switching of energies, i.e., switching between high and low x-ray tube voltage, or by affecting the detector, e.g. selecting only one energy level during a particular study, or a combination of source and detector.

In the preferred embodiment, a dual energy x-ray beam is used for the measurements of bone character (i.e. BMC and BMD) whereas a single energy x-ray beam is used for automated morphometric measurements. It has been determined that the single energy beam provides greater precision (i.e. higher data density per pixel) in the resulting scan than a dual energy system. However, the novel features of the invention can also be combined with the features of strictly dual energy x-ray densitometers to permit measurement of the morphometry as well as the bone density of the subject. Alternatively, a single energy beam may be used alone for morphometry measurements without densitometry measurements.

For purposes of illustrating the present invention, a study of the morphology of a human vertebra and other bones will be described. It should be understood, however, that the invention is not limited to studies of humans but can be applied to animals as well as humans.

The digital x-ray device 10 of the preferred embodiment also has the capability of selecting between a fan beam 23 of x-rays which is collimated and oriented toward the vertebra such that the plane of the fan beam 23 is perpendicular to the longitudinal axis of the spine, or a pencil beam being substantially the centermost ray only of the fan beam 23 along the radiation axis 24. When the fan beam configuration is selected, the detector 13 is a linear array of detector elements subtending the fan beam 23 for providing simultaneous measurements along a number of rays of the fan beam 23 associated with each such detector element. When the pencil beam configuration is adopted, only a limited number of detector elements 13' are employed and measurement is made only along the single ray of the pencil beam. A cone beam (not shown in FIG. 1) may also be used, in which case the detector 13 is a matrix of rows and columns of detector elements covering the area of the fan beam 23 opposite the patient 16.

The fan beam 23, when used, is scanned along the longitudinal axis of the spine or scanning direction 19. The use of a narrow fan beam 23 perpendicular to the spine allows imaging of the spine, or other long bones generally aligned with the spine such as the femur, with minimal distortion along the longitudinal axis resulting in the ability to measure vertebral dimensions in this axis with greater accuracy than possible with a cone beam. For greater accuracy in the horizontal axis, the fan beam 23 may also be oriented so that the vertebral body or other bone is irradiated by the center portion of the beam rather than the edges which are subject to distortion. Since the center of a fan beam 23 has little angulation, the resulting data is comparable to that obtained with a pencil beam and yet a scan can be obtained much faster.

Alternatively, when the pencil beam is used, a raster scan 17 of the lateral view of the vertebral body is done. The raster scan moves the radiation axis back and forth in the anterior-posterior direction along successive scan lines separated in the longitudinal direction so that the radiation axis moves generally along the scanning direction 19. The raster scan 17 results in the slower acquisition of data but provides the least distortion from parallax.

If a cone beam is used, the digital output must be reformatted to compensate for ray alignment in order to allow more accurate measurement of dimension. The cone beam acquisition may be performed at discrete stationary locations or may be acquired continuously as the radiation axis 24 is scanned along the scanning direction 19.

The rotatable C-arm 14 carrying the radiation source 12 and the detector 13 is connected to, and operates under the control of, a general-purpose digital computer 18 which is specifically programmed for use in operating the digital x-ray device 10 and analyzing the data and includes specialized algorithms for carrying out the calculations required by the present invention. In addition, the present invention includes a data acquisition system ("DAS") and a data storage device (both of which are not shown) and may be included in the computer 18 and a display 22 for outputting the data analysis.

Figure 11:
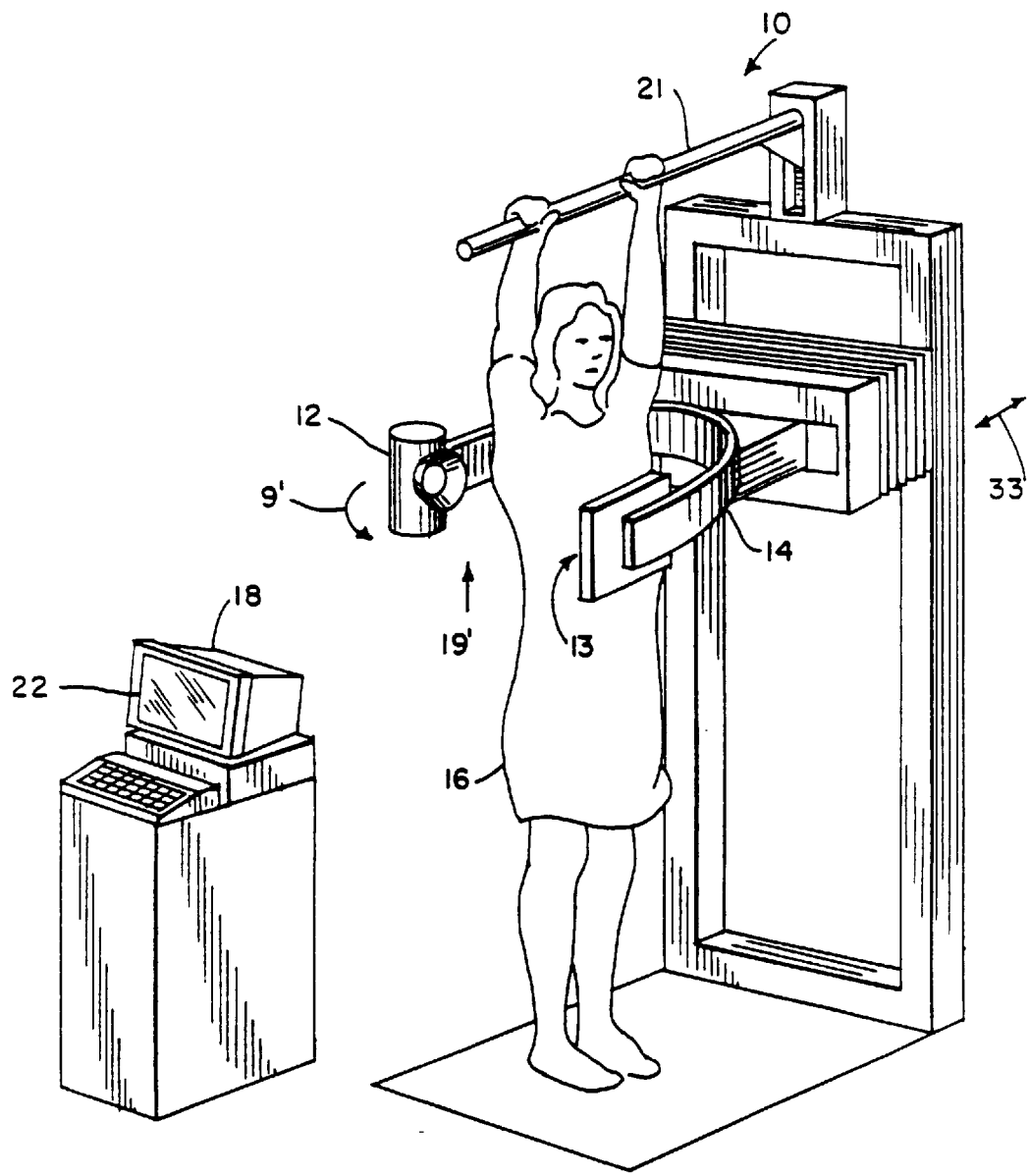
FIG. 11 is a schematic illustration of an instrument for use in the present invention showing a third embodiment in which the patient is scanned in a standing position.

Referring now to FIG. 11, in a second embodiment of the digital x-ray device 10' preferable for use in studies where the patient's spine and other bones should be under the natural load imposed by the weight of the patient's body, the patient 16 remains in a standing position with the hands above the head resting on a horizontal grip bar 21 positioned above the patient's head. The grip bar 21 serves to position and stabilize the patient between the source 12 and detector 13. In this embodiment, the source 12 and detector 13 rotate about a vertical axis and the C-arm 14 on which they are mounted rotates in a horizontal plane as indicated by arrow 9'.

The C-arm 14 may be moved vertically along the patient's body as indicated by scanning direction 19' and may be translated in a horizontal plane as indicated by arrow 33 to provide complete flexibility in allowing overlapping scans of the patient 16 for studies that involve a wider path than is subtended by the detector 13. In other respects, the vertically oriented digital x-ray device 10' operates analogously to its horizontal counterpart shown in FIG. 1.

A single digital x-ray device 10 may be advantageously employed for both standing and supine studies of the patient 16 by incorporating a pivot (not shown) in the supporting structure of the digital x-ray device 10 so that it may swing from the vertical position of FIG. 11 to the horizontal position of FIG. 1 for the different types of studies. It will be understood to those of ordinary skill in the art that the other components of the devices of FIG. 1 and FIG. 11 are common to both machines and thus that this pivoting design may provide a flexible, cost effective single machine.

In most general terms, the radiation source 12 emits radiation of a certain energy level or levels along the radiation axis 24 at defined locations along the scan. The radiation passes through the vertebra 20 being scanned and is then received by the detector 13. The analog output of the detector 13 is sampled and digitized so as to produce a signal consisting of discrete data elements by a data acquisition system ("DAS") which may then transmit the digitized signal to the computer 18 which stores the data in computer memory (not shown) or on a mass storage device.

Film Cassette

Figure 17:
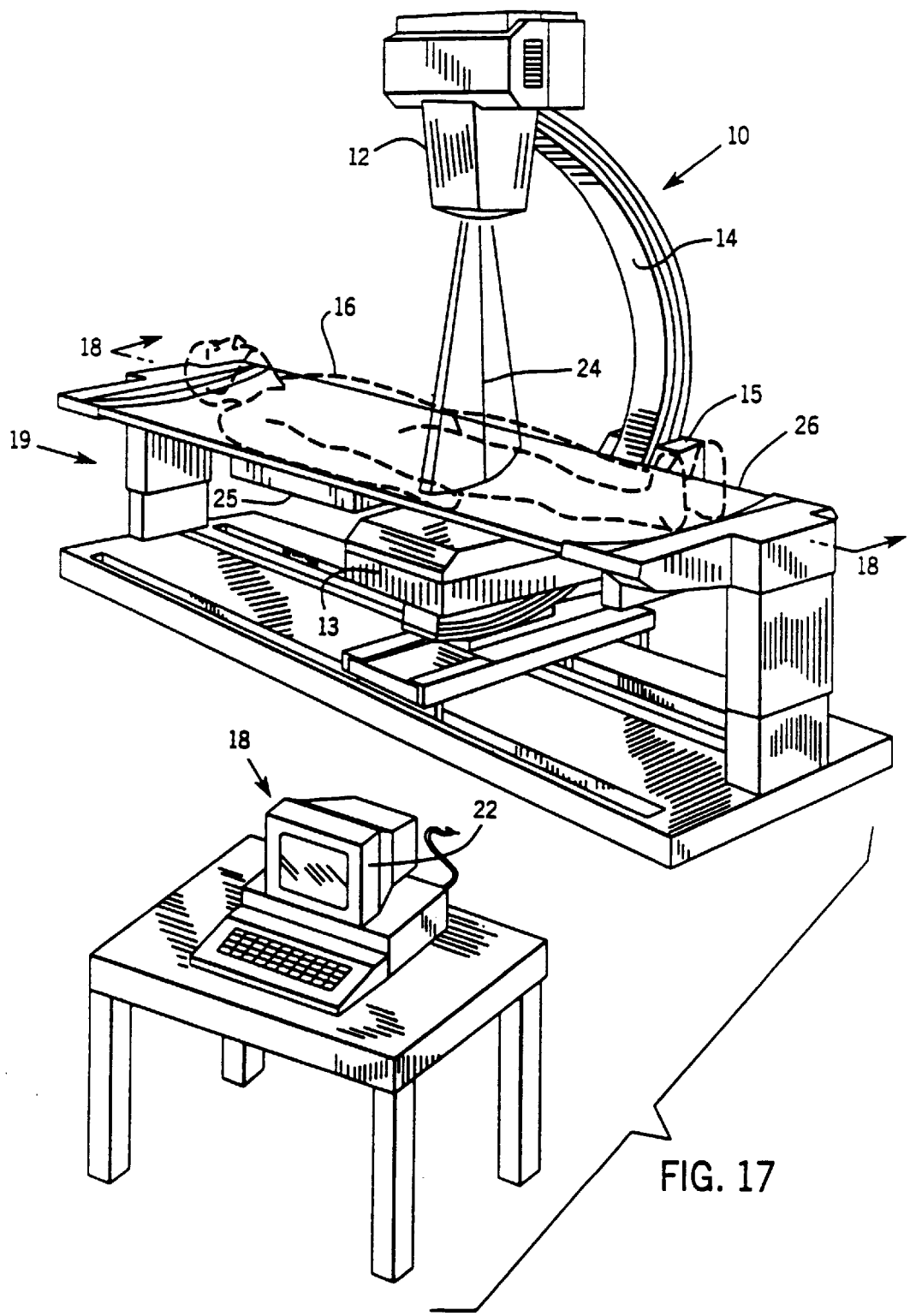
FIG. 17 is a figure similar to FIG. 1 showing the placement of a film cassette beneath the patient table for simultaneously acquiring a digital dual energy density image and an analog radiographic image by means of a scanning fan beam.
Figure 18A:
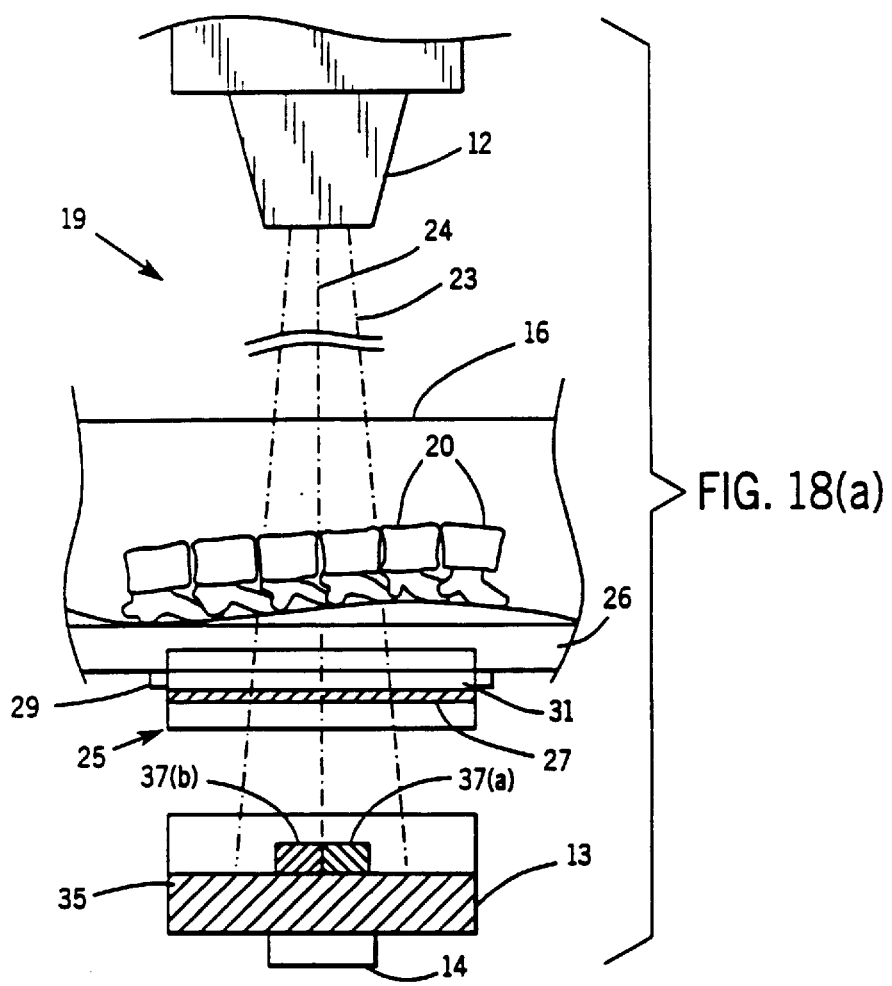
FIG. 18 is a simplified elevational view along line 18—18 of FIG. 17 showing the position of the radiographic film cassette between the dual energy detector and the patient during scanning.
Figure 18B:
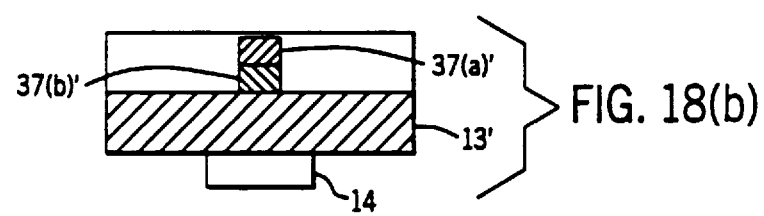

Referring to FIGS. 17 and 18(a) and 18(b), table 26 is constructed of an epoxy impregnated carbon fiber laminated over a foam plastic core or any similar material which provides an extremely light structure that is generally radiolucent and stiff. Importantly, the table 26 provides an extremely uniform attenuation so as to prevent the introduction of artifacts into a radiographic image taken through the table, especially in the vertical or anterior-posterior direction.

A film cassette 25 is mounted on the underside of the table 26 to hold a radiographic film 27 in a generally horizontal plane. The cassette 25 is attached to the table 26 by radiolucent retaining tabs 29 which permit the cassette 25 to be both easily attached to the table 26 and removed from the table 26 to be taken to a darkroom to remove the film 27 so that the film 27 may be developed. In order to conform to the bottom surface of the table 26 which is downwardly convex, the cassette 25 is box-like with a cylindrically concave upper surface that may fit closely to the table 26. By reducing the cassette's displacement from the table 26, more clearance is provided between the cassette 25 and the detector 13.

The film 27, when positioned within the cassette 25, is enclosed in a radiation permeable but light opaque outer casing that permits the film 27 to be handled in normal room light. Preferably, the walls of the cassette 25 are constructed of thin aluminum to provide an opaque and durable enclosure that minimizes the attenuation of the x-rays passing though the cassette 25. Importantly, the entire cassette 25 is constructed to provide both minimal and uniform attenuation to the x-ray beam passing through the patient and the table 26 so that the beam exiting the cassette 25 may be further detected by means of the detector 13. Thus, the cassette 25 includes no beam stopping structure on its lower wall such as may be present in some commercial x-ray cassettes.

A conventional x-ray grid 31 may be positioned above the film 27 to improve contrast by reducing scatter such as is well known in the art. Such a grid may have a lamellae (not shown) that are canted to follow the general angle of the rays of the fan beam 23 from the source 12.

After the fan beam 23 passes through the cassette 25, it is received by the detector 13 which includes an x-ray absorbing stop plate 35 attached to the C-arm 14. The stop plate 35 presents a generally horizontal surface when the C-arm 14 is in the anterior-posterior orientation. On the top of the stop plate 35, toward the patient, are high and low energy detector elements 37(a) and 37(b) forming parts of the linear array of the detector 13 and together subtending the thickness of the fan beam 23.

When the fan beam 23 is poly-energetic, discrimination between high and low energy attenuation of x-rays by the patient can be done by the detector 13 which illustrates side by side linear array detectors. The detector elements 37(a) are selectively sensitive to high energies and detector elements 37(b) are selectively sensitive to low energies. In this case, during the scan along scanning direction 19, each array of detector elements 37(a) and 37(b) forms either a high or low energy image, and these two images are aligned and mathematically combined to produce the necessary bone density information according to mathematical algorithms known in the art.

An alternative design shown in FIG. 18(b) can be a stacked array detector as illustrated in detector 13'. In this arrangement, elements 37(a)' and 37(b)' are selectively sensitive to low and high energy spectrums, respectively. A particular advantage of the stacked array detector is that it can easily accommodate a multi-linear array or area detector design. Such stacked detectors are described and claimed in Barnes, U.S. Pat. Nos. 4,626,688 and 5,138,167, incorporated herein by reference.

During the scanning of the poly-energetic x-ray fan beam 23 across the patient, the x-ray film 27 is also exposed progressively across its surface by the uniform and highly collimated fan beam 23. The collimation of the fan beam 23 reduces scatter and provides accurate edge definition of the vertebra 20.

Generally the low energy x-rays striking the high energy radiation detector 37(a) and the low energy x-rays striking the high energy detector 37(b) are rejected and do not form a useful part of the bone density image. Nevertheless these rays all expose the film 27 and thus are fully utilized in the film image. Importantly, the present invention recognized that, given the quantum efficiencies of the detector 13 and film 27, the interposition of the film 27 and cassette 25 does not significantly increase the exposure time required to acquire the bone density image and thus the film increases the imaging information that may be obtained for a given dose to the patient during a bone density scan.

Once the scan is complete, the signals provided by the detector 13 are reconstructed into an image on the computer 18 and the cassette 25 is removed so that the film 27 may be developed. Because the film 27 is exposed simultaneously with the collection of data by detector 13, the film image may be used to confirm the operation of the scanner and the positioning of the patient. Unlike the bone density image formed from the data from detector 13, the film image is broad spectrum and will closely match the characteristics of a conventional radiograph in terms of contrast and resolution. For this reason, the film image may be preferred by trained radiographers for certain diagnoses. In particular, it should be noted that because the detector 13 necessarily detects a narrow energy range, even a simulated broad spectrum image produced from the data from the detector 13 will not be identical to the image on the film 27.

The film may also be used for archival purposes, eliminating the need for an expensive film printer for producing archival images. Also, the film image may be used for morphometric measurements with the physician measuring relevant dimensions directly on the film typically as illuminated on a light table.

The above described invention of combining a film cassette with a solid state dual energy discriminating detector is subject to many modifications and variations which will become apparent to those of ordinary skill in the art. Not the least of which is the substitution of a computed radiography or stimulable phosphor plate such as that developed by Fuji for the film. Accordingly, it is intended that the present embodiment illustrated herein embraces all such modified forms as might come within the scope of the claims.

Automated Morphometry

Vertebral Studies

Manual measurement of bone morphometry is subject to errors both in the determination of the edges of the bone and the orientation of the measurement between edges. Preferably, therefore, the morphometric measurements are made automatically by computer analysis of the data obtained by the detector 13. Such analyses can apply statistical techniques to multiple data points to provide a more robust and repeatable determination of bone edges and orientations.

Figure 5:
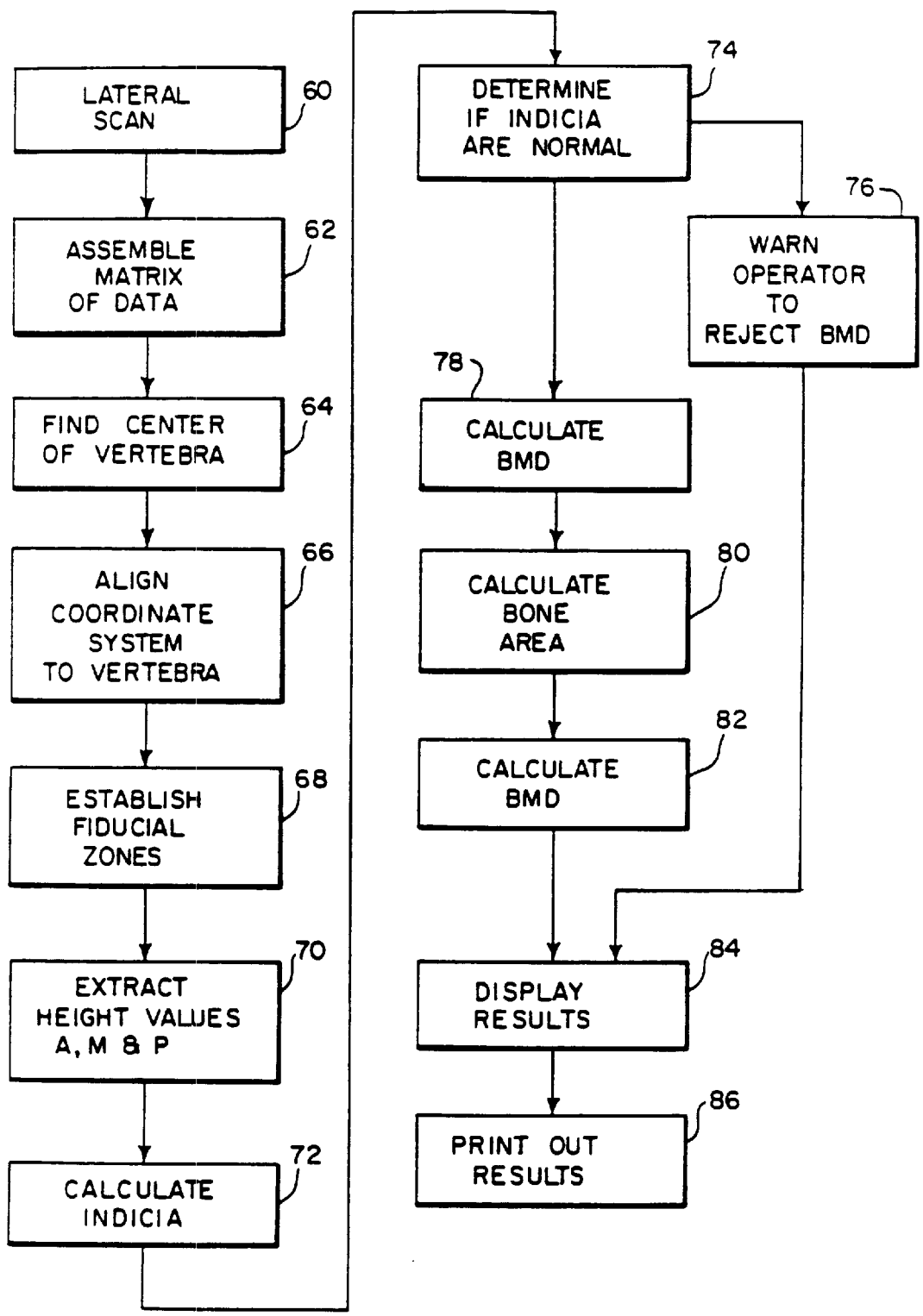
FIG. 5 is a flow chart illustrating the method of the present invention in analyzing vertebral morphology.

Referring now to FIG. 5, upon completion of the scanning of the patient 16 by the source 12 and detector 13 as indicated by process block 60, the computer 18 of the present invention arranges the data elements obtained in the scan in a matrix per process block 62. Each data element of the matrix is associated with a spatial location defined by the position of the C-arm 14 when the data element is acquired during the scan. The spatial locations among the data elements differ by the distance the instrument, e.g., the source 12 and detector 13, moves between taking each data point, both laterally and (in the case of the pencil beam) vertically between scans.

For a digital x-ray device 10 such as that in FIG. 1 which uses a fan beam 23, data elements are taken in a series of scans by moving the x-ray source 12 and detector 13 in short longitudinal steps. If a pencil beam is used, data elements are taken in short vertical scans in the anterior-posterior direction. In either case, the matrix of data elements is assembled from a series of these scans to collect data over an area defined by the length of the scan along the longitudinal scanning direction 19 or the vertical lines of the raster scan 17.

In studying the morphology of the human vertebra, it is preferred that the scan be taken from a lateral direction through the subject's spine and a single energy mode is selected. Each data element has a relative value proportional to the amount of radiation absorbed by the tissue at the corresponding location. In turn, the absorption of radiation by a tissue correlates to certain physical properties of that tissue. For example, bone absorbs a greater amount of radiation than does soft tissue. The data elements thus obtained are referred to PBM for pseudo bone mineral content. The numbers are pseudo values because they are non-calibrated and therefore dimensionless. At this point in the analysis, therefore, only the relative differences between the data elements are significant not their absolute values. While the calibration for each data element could be done at this point, it is consumptive of computer resources, and thus is deferred at this point and the PBM values are used. The matrix of values thus obtained is a representation of the relative density of the patient's vertebra viewed laterally.

Once the matrix is assembled, the computer 18 automatically conducts a local comparison of data elements to determine the juncture of data elements attributable to bone and data elements attributable to soft tissue. In order that the purpose and the results obtained from such a scan may be readily understood, reference is had to FIG. 2 which illustrates an idealized set of vertebrae 20. Each of the vertebrae 20 has characteristic boundary regions indicated by the reference numbers in FIG. 2 with respect to a single vertebra. Each of the vertebrae has an anterior border 30, a posterior border 32, a superior border 34, and an inferior border 36. Additional elements of the vertebrae 20 located rearward of the posterior border are referred to as the posterior elements 38. The region between adjacent vertebrae 20 is referred to as the intervertebral zone and is indicated at 40.

Superimposed on the lowest of the illustrated vertebrae 20 of FIG. 1 is a series of horizontal lines representing the raster scans 17 of the digital x-ray device 10 as employed when the digital x-ray device 10 is operating with a pencil beam. The results of that raster scan is the matrix of digital values with each point value in a single scan being displaced one unit distance from the previous measured digital value.

Figure 2:
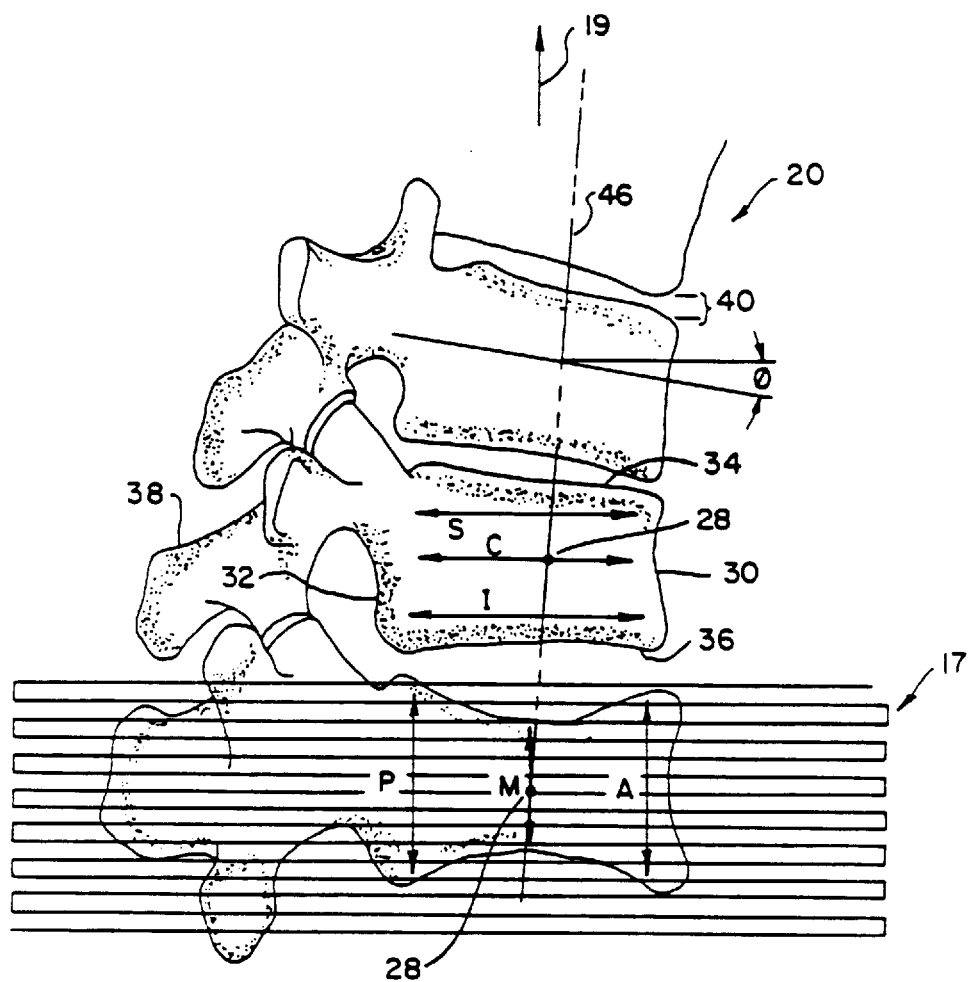
FIG. 2 is an illustration of a lateral view of a vertebra illustrating measurements used in determining indicia used in the present invention.

Referring to FIGS. 1 and 2, the patient 16 is supported in the supine position on a table 26 so that the vertebrae 20 of the spine are generally aligned with the scanning direction 19. Nevertheless, it will be recognized that because of the curvature of the spine, the angle of the vertebrae 20, i.e., the angle of the anterior border 30, a posterior border 32, a superior border 34, and an inferior border 36 with respect to the scanning direction 19 will vary among vertebrae 20. Whereas this variation may be accommodated by the trained eye of a physician in estimating the distances that describe the morphology of the vertebrae 20 for the automation of such measures, the orientation of the vertebra 20 with respect to the raster scan 17 or the scanning direction 19 must be established to provide repeatable and accurate morphology measurements.

The first step in evaluating the relative placement of a vertebra 20, indicated by process block 64 of FIG. 5, is a determination of the approximate location of each vertebrae 20 as identified by its approximate center 28. Preferably, the centers 28 are located by evaluating the horizontal and vertical graphs of FIGS. 3 and 4.

Figure 4:
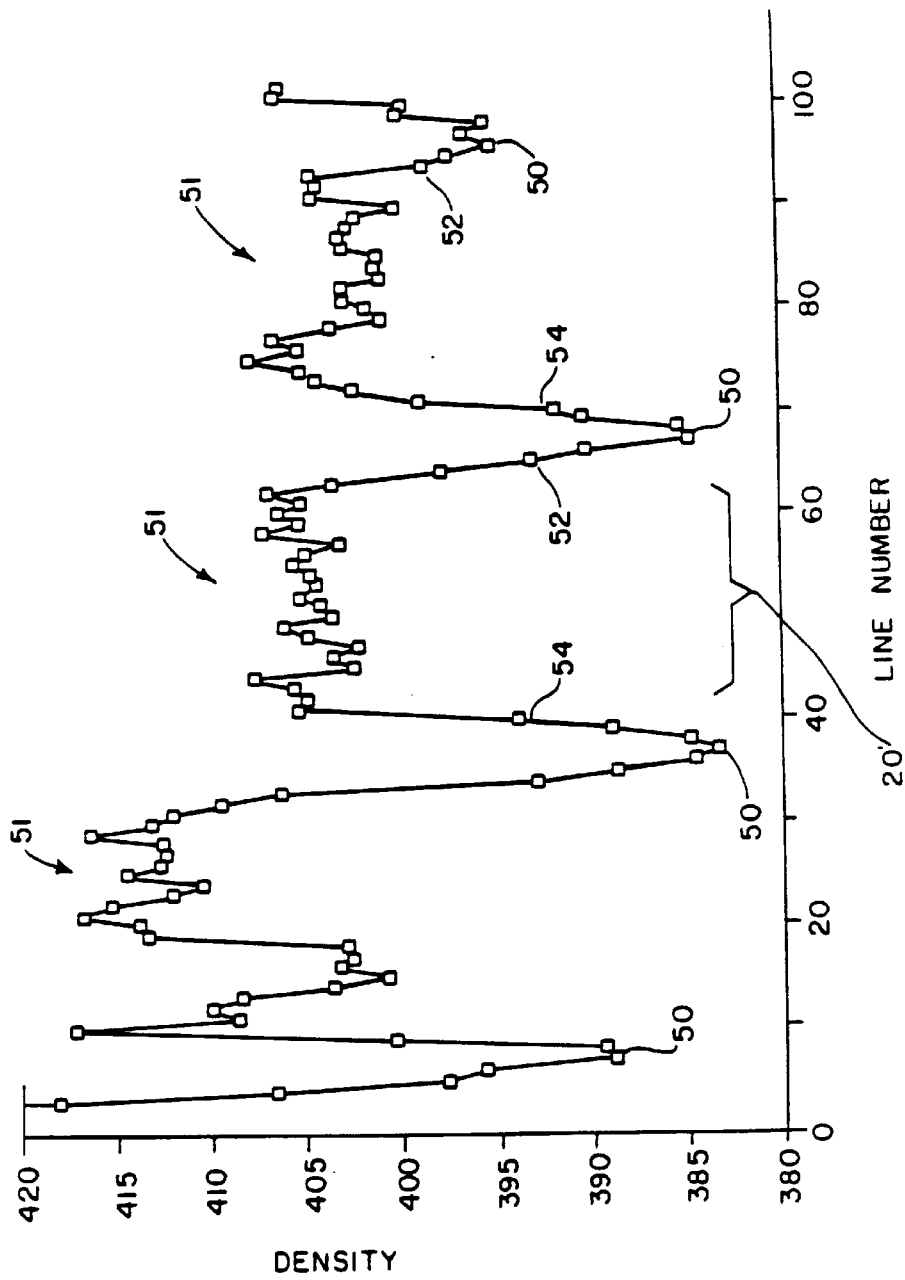
FIG. 4 is a graph plotting bone density versus position in a vertical line across a vertebra.

Shown in FIG. 4 is a superior-inferior graph of the spinal column of vertebrae 20. The vertical axis of the graph represents the units of body density measured at the detector 13 while the horizontal axis represents the spatial locations of data elements along a line such as indicated at 46 in FIG. 2. Ideally, line 46 is centered along the spine as positioned by several arbitrary horizontal graphs of adjacent vertebrae 20 as will be described below. Alternatively, the graph of FIG. 4 may represent not the data elements along a single line 46 but an average of data elements along anterior-posterior lines.

Generally, when a pencil beam is used, the data elements in the vertical graph are not derived from a single line of raster scan 17 of digital x-ray device 10 but rather are reassembled using suitable digital techniques from the entire matrix of data elements collected by the digital x-ray device 10. As reassembled, the values of the graph of FIG. 4 represent a sequential series of data elements taken in a superior-inferior direction. This set of data elements is equivalent to the result which would be obtained from a single superior-inferior scan.

Note that the graph of FIG. 4 includes local minima 50 and local maxima 51. These minima 50 represent areas of low density and the maxima 51 represent areas of high density. The location of the intervertebral zones 40 are readily ascertainable as the local minima 50 and the approximate inferior border 52 and superior border 54 of the vertebrae 20 are recognizable as the portions of the graph on either side of the local minima 50. The superior-inferior centers of the vertebrae may be identified as points halfway between the local minima 50.

Figure 3:
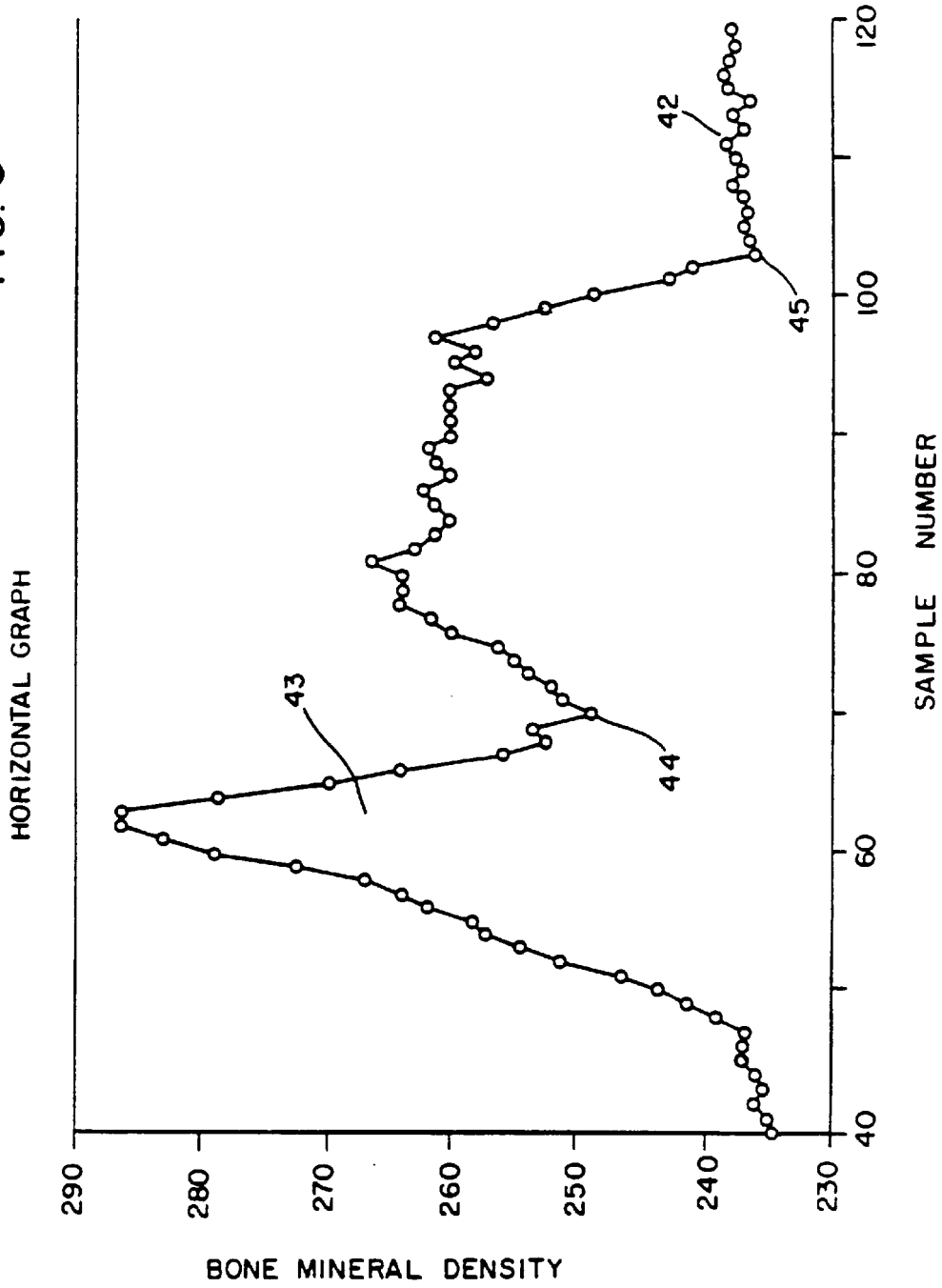
FIG. 3 is a graph plotting bone density versus position in a horizontal scan line across a vertebra such as that illustrated in FIG. 2.
Figure 6:
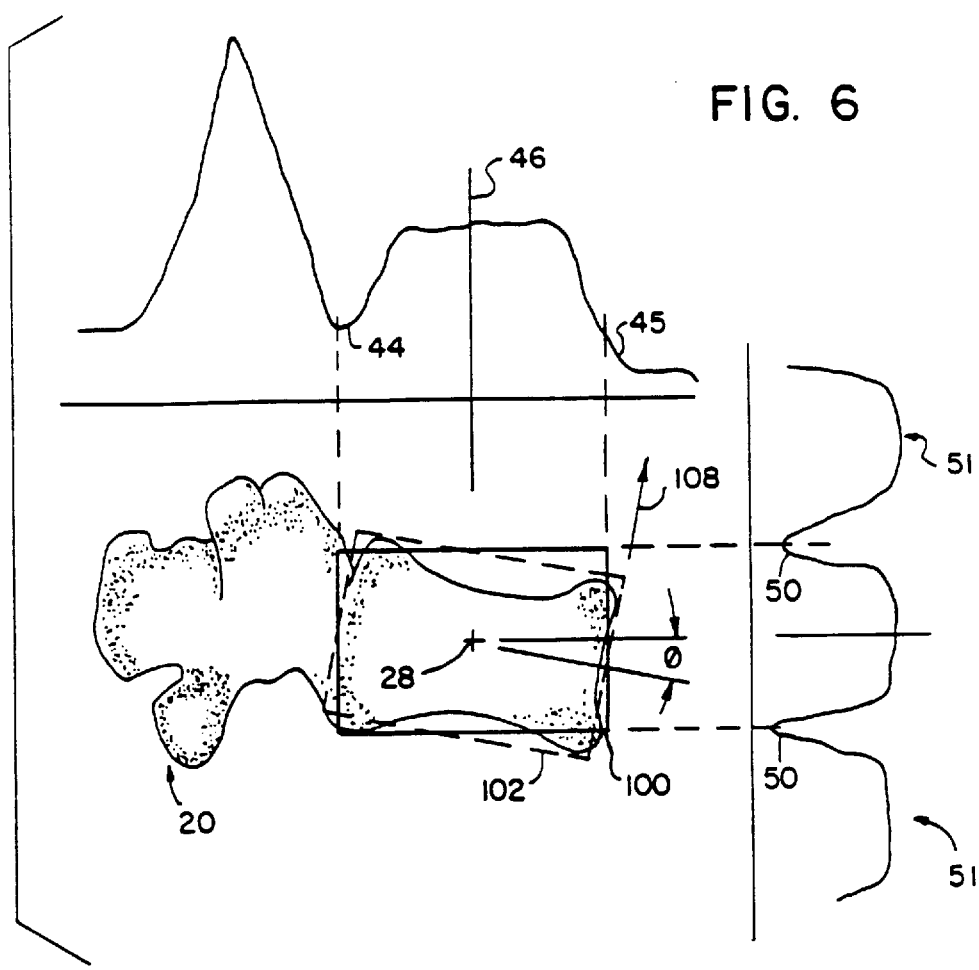
FIG. 6 is an illustration of a vertebra and its vertical and horizontal graphs similar to FIGS. 2, 3 and 4 showing a first method of determining an analysis axis.

Referring now to FIG. 3, a horizontal graph is constructed along each anterior-posterior line of the scan pattern. The horizontal graph of FIG. 3 like the vertical graph of FIG. 4 has, as its vertical axis, bone mineral density. The horizontal axis of the graph of FIG. 3 is the number of an anterior-posterior scan line. Also like the vertical graph of FIG. 4, the horizontal graph has local minima 44. The local minimum 44 represents the approximate posterior border 32 of the vertebra 20 located between the maxima created by the posterior elements 38 and the maxima created by the major portion (i.e. the body) of the vertebra 20 itself. Minimum 45 indicates the approximate anterior border of the vertebra 20. Thus, the center 28 of each vertebrae 20 may be approximated as illustrated in FIG. 6 as the intersection of the scan line in the anterior-posterior direction which is halfway between points 44 and 45 and the superior-inferior center 53 of the vertebra 20 which is halfway between the local minimum 50 of the vertical graph.

Alternatively, in a semi-automatic mode, the centers 28 may be identified interactively by having an operator of the digital x-ray device 10 observe an image produced by representing the matrix of data elements as a series of pixels having gray values in the image proportional to their density values on the display terminal 22. The operator may move a cursor with a track-ball or mouse-type cursor control device (not shown) to position the cursor at the center of the vertebral images so displayed thereby selecting the centers 28. The screen position of the cursor at the time of selection is recorded and related to a spatial coordinate of the discrete data values forming the image, thus relating the selected points on the image to the centers 28 of the vertebra as recorded in the matrix of discrete data.

These centers 28 may be refined by the above described center determining process or used directly for the morphometric measurements to be described below, the latter which intrinsically correct for small errors in the center determination.

Referring now to FIG. 5, once the center 28 of each vertebrae 20 has been detected as indicated by process block 64, a coordinate system is established aligned to each vertebrae 20. Referring now to FIG. 6, a rectangular area 100 may be established about the center 28 of each vertebrae 20 having an anterior-posterior width equal to the distance between minima 44 and 45 and having a superior-inferior height equal to the distance between minima 50. If necessary, the exact dimensions of the rectangle may be adjusted by the operator to conform with the image of the vertebrae as described above. As defined, the rectangular area 100 will be aligned with its sides parallel or perpendicular with the scans of raster scan 17 or the scanning direction 19.

The PBM data elements within the rectangular area 100 are then summed to produce an alignment value. This alignment value indicates roughly the total bone mass of the vertebra 20 within rectangular area 100 and is thus a general measure of the "fit" of the rectangular area 100 to the vertebra 20.

A new rectangle 102 is then created also centered about point 28 but perturbed by angle f and a new alignment value is calculated. If the perturbed rectangle 102 produces a lower alignment value, a new perturbed rectangle 102 is generated with a rotation in the opposite direction. If, however, a higher alignment value is obtained with perturbed rectangle 102, a further rectangle 102 is generated with additional angle f and a new alignment value calculated. This process is repeated until there is detected a decrease (after an increase) in alignment value within the perturbed rectangle 102.

Thus, rectangle 102 is gradually rotated in one way or the other until the alignment value is maximized. It is found that the orientation of rectangle 102 which gives the highest alignment value is also the orientation which maximizes the amount of vertebra 20 contained within borders of rectangle 102. Thus, upon completion of the rotation process, the rectangle 102 is a best fit of a rectangle 102 to the vertebra 20 and establishes a coordinate system for analyzing the vertebra 20 morphology. Specifically, all measurements of the vertebra 20 are taken along parallels to the vertical or horizontal edges of the rectangle 102. A column axis 108 parallel to the vertical edge of rectangle 102 is identified to indicate this axis of measurement as distinguished from the scanning direction 19.

Figure 7:
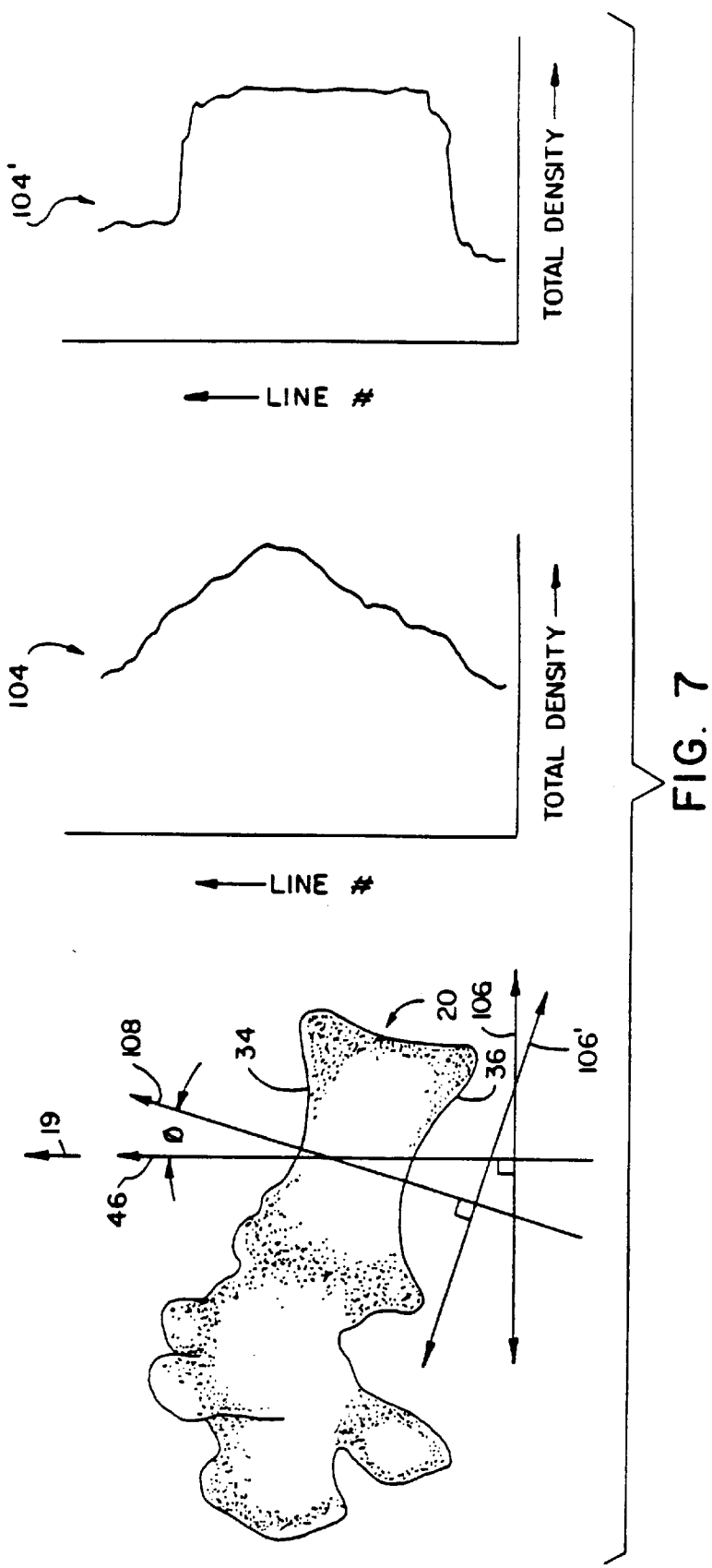
FIG. 7 is an illustration of a vertebra showing corresponding graphs taken along two different axes showing a second method of determining an analysis axis.

Alternatively, and in a second embodiment shown in FIG. 7, the coordinate system for the measurement of vertebral morphology may be established by creating a column averaged graph 104 taken along line 46 in the scanning direction 19. The vertical axis of the column averaged graph is a line number of a row of data elements, and the horizontal axis of the column averaged graph is the total density of the data elements of that row, that is, the sum of the data element in that row. For a vertebrae 20 tipped with respect to the scanning direction 19, the column averaged graph 104 will exhibit a relatively low rate of change as a result of the obliquely advancing rows of data elements extending arrow 106 which crosses the inferior border 36 and superior border 34 at an angle. In a manner similar to that described with respect to FIG. 6, a new column axis 108 is iteratively generated and canted with respect to the scanning direction 19 by an angle f. A new column averaged graph 104' is generated with respect to this column axis 108. If the row orientation 106' of the new column axis 108 better aligns with the inferior border 36 and the superior border 34 of the vertebra 20, the column averaged graph 104' will exhibit a more rapid rate of change in total row bone density with respect to row number. The derivative of the column averaged graph 104' may be taken and the peak value of the derivative compared between column averaged graphs 104 with other column axes 108 (at different angles f) to select a column axis 108 that produces the greatest such derivative value within a limited angular range. This column axis 108 is selected as the reference axis for future morphological measurements.

Thus, although the scan direction 19 may not be aligned with the vertebra 20 so that the anterior and posterior borders 30 and 32 are substantially parallel to the scanning direction 19 and the superior border 34 and inferior border 36 substantially perpendicular to the scanning direction 19, a new column axis 108 may be determined and measurements of the vertebrae morphology taken with respect to that column axis 108 to provide improved accuracy and repeatability in the measurement of the vertebrae morphology. This alignment of a coordinate system represented by column axis 108 to each vertebra is indicated at process block 68 of FIG. 5.

Figure 8:
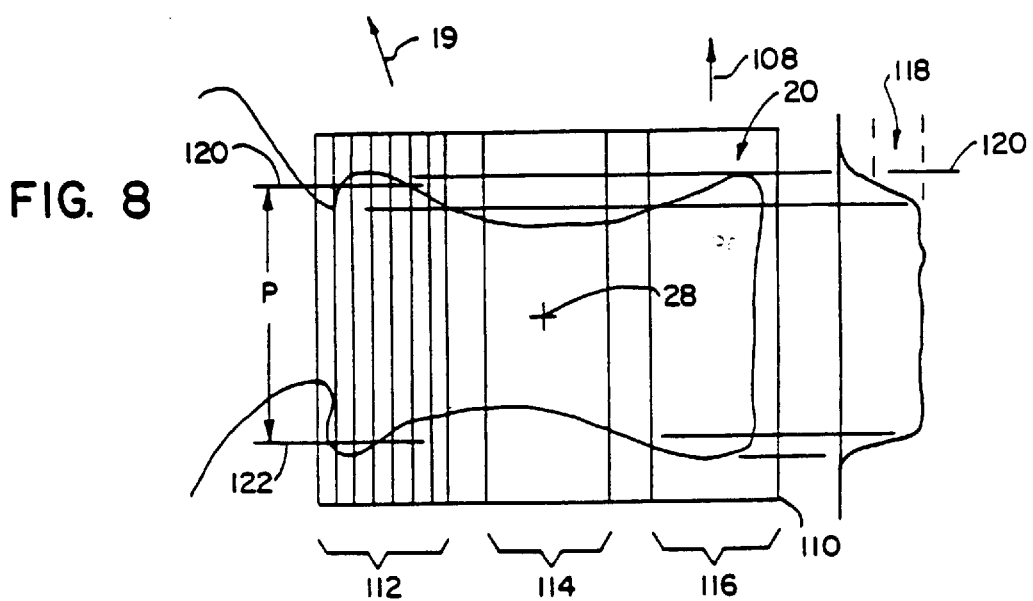
FIG. 8 is a lateral view of a vertebra aligned with the analysis axis showing the generation of measurement zones over which vertebral height is averaged in preparation to analyzing the morphometry of the vertebra.

Referring now to FIG. 8, in general, the column axis 108 will differ from the scanning direction 19. Once the column axis 108 has been determined for a given vertebra 20, the data elements are effectively "rebinned" to comport with that new coordinate system. The rebinning may be accomplished by generating a new series of locations within the vertebra 20 corresponding to evenly spaced lines and columns aligned with the new column axis 108. Interpolated data elements lying on these locations at the new columns and rows are obtained by a bi-linear interpolation of the nearest neighbor actual data elements weighted according to the actual locations of those data elements. New vertical and horizontal graphs are then constructed from these interpolated data elements much in the manner as described with respect to FIG. 6 with the horizontal graph displaying average density for a vertical column of interpolated data elements and the vertical graph displaying the average density for a row of the interpolated data elements.

Referring to FIG. 8, the minima of the horizontal and vertical graphs are used to derive an analysis rectangle 110 in the same manner as that described with respect to the rectangular area 100 of FIG. 6, the analysis rectangle 110 being aligned with the column axis 108 and encompassing principally the vertebra 20 and not the posterior elements 38. This analysis rectangle 110 is then divided by the computer into zones as indicated by process block 68 of FIG. 5. In the preferred embodiment, three zones are selected, a posterior zone 112, a medial zone 114, and an anterior zone 116. In the preferred embodiment, the zones are rectangular having an anterior to posterior width of ¼ that of the analysis rectangle 110 and extending the full height of the analysis rectangle 110 in the superior to inferior direction and evenly spaced therein. The relative width and number of zones is arbitrary and can be varied according to the needs of the user and the dimensions of the analysis rectangle 110. Alternatively, in a semi-automatic mode, the measurement zones may be determined interactively by an operator who indicates general regions on an image of the data as described above where data within those regions is to be analyzed.

In the example of FIG. 8, the posterior, medial and anterior zones define a set of data elements that will be employed to produce fiducial measurements with respect to the morphology of the vertebra 20. The first set of such measurements is to determine the average height of that portion of the vertebral body in the superior to inferior direction of each of the three zones of the analysis rectangle 110.

In one embodiment, this is done by starting with the posterior zone 112; the data elements within the zone are automatically summed across rows by the computer to produce a zone graph 118. The vertical axis of the zone graph 118 is a row number of data elements corresponding to an anterior-posterior row and the horizontal axis is the total bone mass of the data elements of that row and within the posterior zone 112. This zone graph 118 differs from the other graphs described thus far in that it is effectively focused on the posterior zone 112 and thus sensitive to the morphology of that region alone.

A first row 120 is automatically identified by the computer on that graph, and thus with respect to the vertebra 20, at the rising edge of the graph 118 associated with the superior border 34 in the posterior zone 112. A number of criteria may be employed in selecting this first row 120 such as the first row having a bone mass value to exceed a fixed predetermined threshold. In the preferred embodiment, the row is selected as that which has a PBM value first exceeding 30% of the peak graph value of the zone graph 118. Ideally, the computer selects as a first row 120 the row which best approximates the position of the superior border 34 if the position of its contour in the posterior zone (as weighted by PBM value) were averaged out. In actual practice, a deviation of the selected first row 120 from the true average of the superior border 34 is not significant as long as the same criteria is used each time in selecting the first row 120 and hence constancy of measurement is obtained.

Likewise, a second row 122 is selected from the graph 118 in its inferior border 36 in the posterior zone 112. Here, the falling edge of the graph 118 is examined and the second row 122 selected as that row which first falls below 30% of the maximum PBM value for the graph 118. The distance between these rows 120 and 122 is automatically determined and termed the posterior height and represented by P and is assumed to be the average height of the vertebral body in the region of the posterior zone.

Each of the other zones, the medial zone 114 and the anterior zone 116, are likewise analyzed by generating a zone graph 118 and identifying two rows, one at the superior border 34 and one at the inferior border 36. The distance between these columns for the medial zone becomes the medial height M and for the anterior zone becomes the anterior height A. The extractions of these morphological height values is indicated in FIG. 5 as process block 70.

In the preferred embodiment, the height values A, M, and P are calculated by multiplying the number of rows of data elements between the first row 120 and the second row 122 for each zone by the distance between each row of data elements in the analysis rectangle 110. That distance between rows of data points is a characteristic of the digital imaging technique used, and will be known. The computer will automatically perform the above described analysis on each zone of the analysis rectangle.

Figure 9:
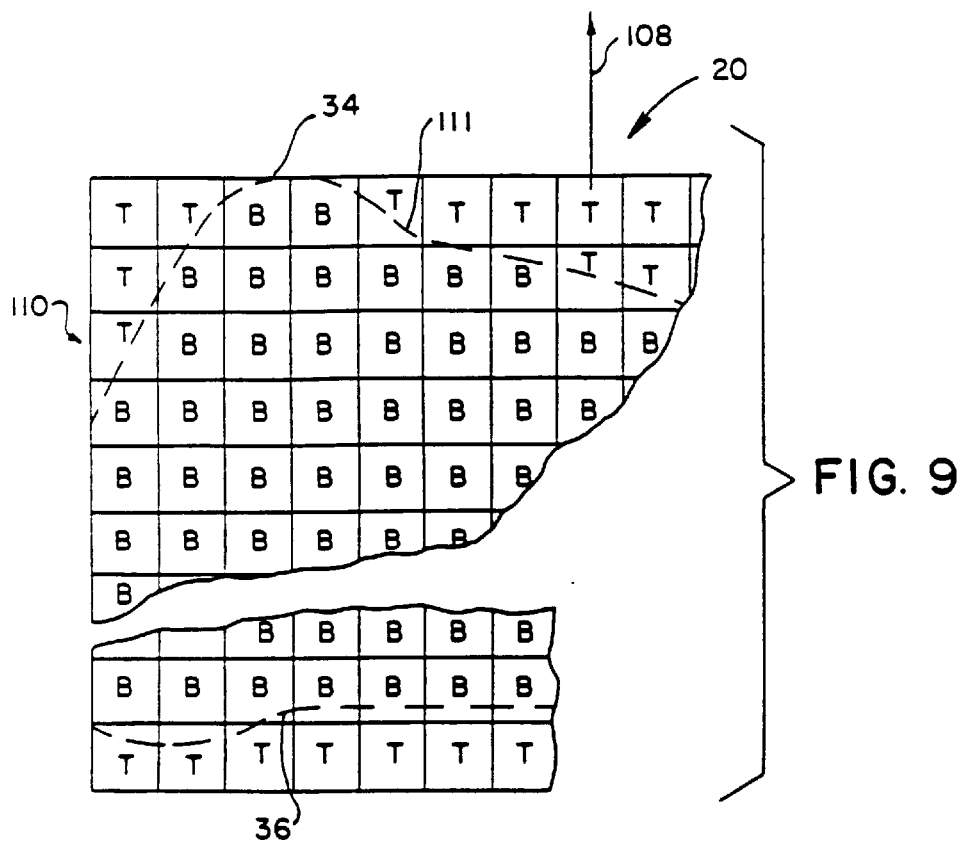
FIG. 9 is a schematic diagram of the bone mineral density values over a portion of a vertebra illustrating one method of determining the borders of a vertebra wherein, for clarity, the density values within a range associated with tissue are shown by the letter "T" and the density values in a range indicating bone are shown by the letter "B"

In an alternative embodiment, the average height of each zone is determined by the computer by automatically identifying in each zone, data pairs; one data element of each pair corresponding to a location on the superior border and the other data element corresponding to a location on the opposite, inferior border. The two data elements of each pair have a relationship to one another such that an imaginary line transecting each data element of a data pair would be reasonably parallel to the column axis 108. Each data element of a data pair is selected by the computer by performing a local comparison of the PBM values of data elements. For example, in selecting data elements lying on the superior border, the computer would examine the PBM values of adjacent elements. As illustrated in FIG. 9, a data element 111 having neighboring data elements of similar value in the anterior, posterior and inferior orientations but of markedly lesser value in the superior orientation, would be assumed to lie at or near the superior border. In like manner, the computer will automatically examine all the data elements in the top ⅓ position of zone 112 to determine those data elements lying on the superior border. Once data elements on the superior border have been selected, a similar analysis would be conducted on the data elements in the lower ⅓ portion of zone 112 to select data elements lying on or near the inferior border portion of zone 112. With data elements selected on each border, the computer would then pair data elements on the superior border with data elements on the inferior border by assigning the data elements to columns reasonably parallel to column axis 108. Having organized the data elements into pairs and assigned the pairs to columns, the computer employs an algorithm to automatically determine the distance between each data element in a pair by multiplying the number of data elements found between each data element of a data pair by the distance between each data element. As stated above, the distance between data elements is a characteristic of the digital imaging technique used. The distance between data elements of a pair is taken as the inferior to superior height of the vertebra 20 at the particular location of the column associated with that pair.

Having determined the height of all the columns in zone 112, the heights are summed and an average height is obtained for zone 112. In similar fashion, average heights are obtained for the medial zone 114 and the anterior zone 116.

By a similar process, the analysis rectangle 110 may be divided into several (preferably three equal) horizontally extending fiducial zones (not shown) and columns identified at the anterior and posterior borders 30 and 32 of the vertebra 20 to determine the average widths of such horizontally extending fiducial zones. In the preferred embodiment, three zones, a superior zone S, a central zone C and an inferior zone I are selected and automatically measured.

In each zone S, C and I, an anterior column and a posterior column is identified in a process analogous to that described above with respect to the selection of the first and second rows 120 and 122 of a posterior zone 112, a medial zone 114 and an anterior zone 116. A center column is also determined for the zones S, C and I being exactly half way between the anterior and posterior identified columns. The intersection of the identified columns of the zones S and I and the rows posterior zone 112, a medial zone 114 and an anterior zone 116 define a set of fiducial points. For example, the intersection of the first row 120 for the posterior zone 112 and the first column for zone C defines one such fiducial point.

The identified columns of the zones S, C and I also serve to create measures S, C, and I corresponding to measures A, M, and P, as described above, but extending in an anterior-posterior direction.

Thus it will be understood that fiducial points at the "corners" and center superior and inferior borders 34 and 36 of the vertebra 20 may be established and that the separation of these fiducial points with respect to one another measured automatically. Although each of these fiducial points has a specific location, they represent an average of the BMD values of the surrounding data points and hence are robust against small errors in the BMD measurements at any given data point.

Once the computer has identified these fiducial points, the computer automatically uses this data to accurately define the shape and size of the vertebra being studied which, at the option of the operator, can be displayed visually such as on a CRT device or a printing device. More importantly, however, the computer is programmed to use the data regarding shape and size to formulate indicia of vertebral condition having clinical or diagnostic value and then to visually display the indicia for use by the operator either in diagnosing a clinical condition or increasing the accuracy of bone density measurements if such measurements are being made.

Using the invention described herein, measurements can be automatically obtained for a single vertebra, or can be obtained for several vertebrae. It is possible to use the analysis performed by the algorithm for several purposes. This analysis is most effectively directed to the vertebral body, that is, the portion of the vertebra excluding the posterior elements. Various measurements of a vertebral body which are obtained by the invention herein described can be used to provide indicia of disease or deformity as described below. Additionally, the measurements obtained of a single vertebral body can be compared to those of adjacent vertebral bodies, as determined from a single scan, to determine if one or more vertebra has been subjected to a trauma or other incident which produces an abnormality in that vertebra. Alternatively, the indicia of a vertebral body can be compared to those obtained from a normal reference population to determine aberrant or abnormal vertebrae, either singly or collectively, in a given patient. Such normative results may be adjusted for body height, sex, and weight of the individual patient as well as for maturity of the individual with the various normals being held in a database. Another alternative is that the indicia for the vertebral bodies can be compared from time to time in the same individual to show changing vertebral morphology over time which can be indicative of the progress of clinically significant conditions.

EXAMPLE 1

Anterior Height

A particular indicia of interest for vertebral morphology is anterior height of the vertebra. It has already been described above in connection with the description of the fiducial points how the algorithm automatically calculates the distance from inferior border to superior border for each fiducial zone. The anterior height of the vertebral body is the distance between the two end plates, or the distance between the superior border and the inferior border at or adjacent to the anterior border. In the prior art, the point at which the anterior height of the vertebra was preferably measured was within the first 5 to 10 mm from the extreme anterior border of the vertebral body. In the preferred embodiment of the present invention, an anterior zone 116 is selected which occupies the anterior ¼ portion of the analysis rectangle 110 and within this zone the computer determines an average height of the anterior portion of the vertebra 20. If compared with the prior art technique of selecting a particular point for measurement of anterior height, the technique of the present invention, which automatically determines an average height within a preselected fiducial zone, is found to be superior in terms of reproducibility. This anterior height A, as determined by the present invention, may be displayed to an operator in absolute units of measurement, such as millimeters, or the computer can provide height relative to the average height either of normal values of vertebrae in the general population or the other vertebrae of that patient.

EXAMPLE 2

Posterior Height

Another indicia of interest is the measurement of posterior height P of the vertebra. Like anterior height, posterior height measurements made in the prior art are taken at a single location within 5 to 10 mm of the posterior border of the vertebra. The present invention provides an automatic measurement of the average height of the posterior region of the vertebra 20 lying within the posterior fiducial zone 112 which occupies the posterior ¼ of the analysis rectangle 110. Like anterior height, posterior height may be displayed to an operator in absolute units of measurement, such as millimeters, or the computer can provide height relative to the average height either of normal values of vertebrae in the general population or the other vertebrae of that patient.

EXAMPLE 3

Anterior/Posterior Height Comparison

An important indicia which the computer can be programmed to automatically obtain is a comparison of anterior height A to posterior height P. Typically a 15% decrease in anterior vertebral height, either relative to a norm, relative to the same individual in previous measurements, or relative to the posterior height of the same vertebra, is taken as an index of anterior vertebral fracture, a clinically significant indication.

EXAMPLE 4

Wedge Angle

Another indicia of vertebral morphology which can be automatically obtained with the present invention is the wedge angle. The wedge angle of the vertebra is defined as the degree of departure from a parallel relationship that linear extensions of the planes of averages of the inferior and superior borders would create. In the prior art, this is calculated based on the overall anterior and posterior height of the vertebra. From these values of anterior and posterior height and from the distance between the locations at which the measurements were taken, it becomes possible to calculate the angle between hypothetical straight lines extending through the superior and inferior borders of the vertebra.

In the present invention, the distance between A and P for purposes of plotting the wedge angle is C. Since A, P and C are average values, variability in the wedge angle due to variation in the selection of the location for height and width measurement is avoided. Typically a 15° wedge angle of a vertebra is taken to indicate that wedge fracture has occurred in the vertebra. A wedge fracture is a recurrent clinical condition observed as a modality of vertebral fracture recognized in clinical literature.

EXAMPLE 5

Biconcavity Index

Another indicia of vertebral morphology which the computer of the present invention can be programmed to automatically measure is referred to as the biconcavity index. The index of biconcavity of the vertebral body is calculated by comparing the degree to which the height of the central portion of the vertebral body deviates from the average height of the posterior and anterior borders of the body. In other words, this is measuring the deformation of the vertebral body as it tends to become a concave object. This biconcavity indicates a degree of deformation of the vertical body associated with relatively poor vertebral condition. This quantity can be calculated automatically by the computer which uses an algorithm to compare M to the average of A and P. M can also be compared to adjacent vertebrae, or to average values from a normal reference population previously obtained. A 15% preferential decrease in central height of the vertebral body as compared to the anterior and posterior borders is often taken to represent a central fracture or a condition of biconcavity.

EXAMPLE 6

Hypertrophy

Another indicia of vertebral morphology which the computer of the present invention can be programmed to measure is hypertrophy of the end plates of the vertebrae or hypertrophy of nodes located within the vertebra. Hypertrophy refers to a condition where portions of the vertebral body have a relative density which is abnormally greater than that typically seen with other vertebrae. In conventional densitometry, localized areas of high or low density are ignored and only larger area averages are obtained. This can lead to misleading interpretations of bone mineral levels when discontinuities are present as caused by hypertrophy. The ability of the present invention to define and reproducibly locate a variety of zones: the posterior zone 112, the medial zone 114, the anterior zone 116 and zones S, C, and I, allow bone density to be evaluated separately at a variety of places within the vertebra. By comparing the bone density in S or I zones to the C zone, for example, end plate hypertrophy may be detected. Alternatively, a hypertrophied node may be detected by evaluating the bone density over the entire region within the fiducial points at the "corners" of the vertebra to identify any data points, or a small set of data points within that defined area that have values which differ by more than a predefined amount from the statistical norm of all the values within that area.

While this indicia is not generated specifically for clinical value in and of itself, it is useful insofar as it represents information about a region of vertebra having unique characteristics which must be excluded from otherwise valid measurements of bone density or mineral content. For this reason, it may be used to provide a warning to the operator indicating that the bone mineral data for a particular vertebra may need close review.

EXAMPLE 7

Intervertebral Spacing

Intervertebral spacing may be readily determined from the evaluation of the fiducial points at the superior border of one vertebra and the inferior border of the next superior vertebra. Essentially, the intervertebral spacing is the distance between the corresponding fiducial points for these two vertebrae.

As a result of the possible difference in column axes 108 for the two vertebrae, the intervertebral distance may preferably be evaluated by considering the average distance between two edges, one defined by line segments joining the fiducial points at the superior border of the inferior vertebra, and the other defined by line segments joining the fiducial points at the inferior border of the superior vertebrae.

EXAMPLE 8

Warning of Defective Vertebra

It is specifically intended that the indicia of morphological character of the vertebral body, whether height, compression, wedge, or biconcavity, are utilized by the instrument for two discreet purposes. One purpose is to create a warning to the operator that the bone mineral density data for a particular vertebra should not be utilized since it may be inappropriate. It can readily be understood that a porous bone, if crushed, will have a higher measured density than a porous bone which has not been subject to crushing. In that instance, the higher density of the crushed bone is not an indication of the health of that bone, quite to the contrary. Accordingly, it is appropriate for the instrument of the present invention to create an indicational warning to the operator as indicated by process block 76 in FIG. 5 when one or more of the indicia of significant vertebral body fracture have been detected. In any event, the result is that a heightened accuracy of bone mineral density calculation is obtained by the bone densitometer as well as providing the benefit of potential diagnosis of clinically significant conditions of vertebral deterioration.

The calculation of these various indicia from the measurements of A, M, and P, and S, I and C and their separation is indicated in process block 72 of FIG. 5. At subsequent process block 76, an indication may be presented to the operator of abnormal indications which have been detected by the method, if any. The abnormal conditions can be indicia described above which are outside the normal values to be expected for patients of the category of the patient who has been scanned. If such an indication has occurred, the operator will then know that the average value for bone density for the particular vertebrae having the discontinuity should not be utilized for clinical purposes.

EXAMPLE 9

Predicting Vertebral Fracture

A decrease in bone mass, or the presence of one or more vertebral fractures, is associated with an increase in the likelihood of future vertebra fractures. A decrease in bone mass of two standard deviations is associated with an increase of four to six times in the likelihood of future vertebral fractures whereas the existence of two fractures, as determined by a morphologic measurement of anterior height or A is associated with an increase of twelve times in the likelihood of future vertebral fractures. See, Ross, et al., "Pre-Existing Fractures and Bone Mass Predict Vertebral Fracture Incidence in Women", *Annals of Internal Medicine*, v.114–11:919 (1991).

A combination of bone mass measurement and morphometric evaluation of fracture is associated with an increase of seventy-five times in the likelihood of future vertebral fractures and provides correspondingly improved predictive power. The present invention, which allows a densitometer to be used in making morphometric measurements, should prove valuable in conveniently providing both bone mass and fracture data for such combined measurements

EXAMPLE 10

Dual Angle Morphology and BMD Measurement

Figure 10:
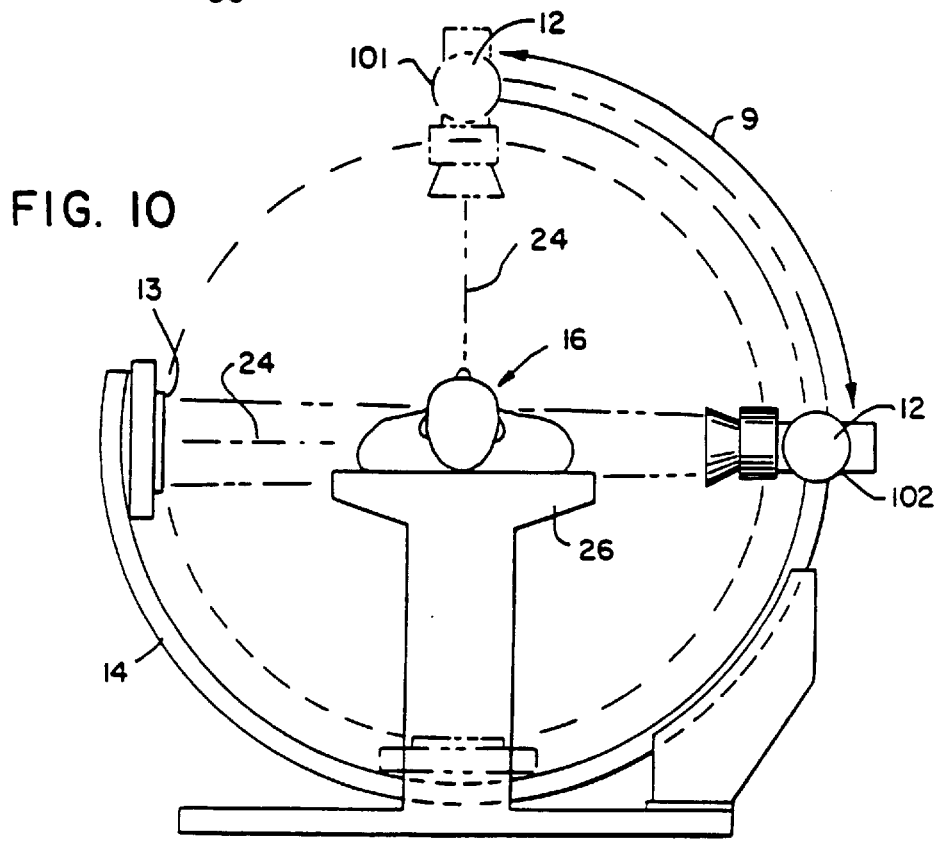
FIG. 10 is an elevational view of the instrument of FIG. 1 viewed along the scanning direction showing movement of the source and detector between a lateral position and an anterior-posterior position in one embodiment of the present invention.

Referring to FIG. 10, prior to the lateral scan of the patient 16, an anterior-posterior dual energy scan may be performed with the x-ray source 12 in position 101 as rotated about the patient 16 on C-arm 14. As is understood in the art, dual energy scanning provides an improved ability to distinguish between x-ray attenuation caused by tissue as opposed to bone allowing more accurate BMD determinations, but also provides less accuracy for morphology measurements. The anterior-posterior positioning of the C-arm 14 also improves the bone density measurement to the extent that the amount of intervening tissue is reduced at that angle.

Referring also to FIG. 5, the BMD values obtained from the anterior to posterior scan may be employed to calculate BMD as indicated by process block 78 and to calculate bone area as indicated by process block 80 according to techniques well known in the art. Rather than directly displaying the BMD values however, a lateral scan is then performed with the x-ray source 12 at position 101 so that the radiation axis 24 is horizontal. The calculated values of BMD for various points in the anterior-posterior scan of the patient may be matched approximately to those corresponding points in the lateral scan and the indicia of the morphometric measurements of a given vertebra 20 may be matched to the calculated BMD values of process block 80 and bone area values of process block 82. If the indicia for a given vertebra are abnormal, then at process block 84, where BMD and area calculations may be displayed, a suitable warning may be given to the operator that the BMD values and area values are suspect as indicated by process block 76.

The correlation of anterior to posterior scanned points to lateral scanned points simply matches the longitudinal coordinates of each such point and makes the assumption that the patient has not shifted on the table appreciably between scans. Alternatively, the intervertebral zones 40 may be derived for each of the anterior-posterior and lateral scans and the data from each scan shifted to correlate the graphs of each scan so that the intervertebral zones 40 match.

The ability to use a densitometer to make morphologic measurements is critical to this augmentation of BMD and bone area calculations by morphometric indicia as it allows both measurements to be made without shifting the patient.

The indicia calculated at any one time for a patient may be compared to subsequent or previous determinations on the same patient. By such comparison, changes in vertebral morphology over time can be tracked. In addition, the digital image obtained at subsequent determinations following an initial determination may be subtracted from the stored initial image to produce a differential image. The boundary conditions used for determining morphological indicia may be used to precisely overlap such sequential images.

Alternatively, the indicia calculated for a patient may be compared to values contained in a data base of reference values categorized by sex, age or other criteria.

The following embodiments illustrate the use of the invention to make morphological measurements of the femur, hip joint, and metacarpal bones of the hand. It is to be understood that these examples are illustrative only and do not limit the invention in any way. In particular, it should be appreciated that the measurements described for the femur and metacarpal may be applied to other bones and joint spaces, such as the shoulder for example, in a human being or an animal body.

Femoral Studies

Figure 12:
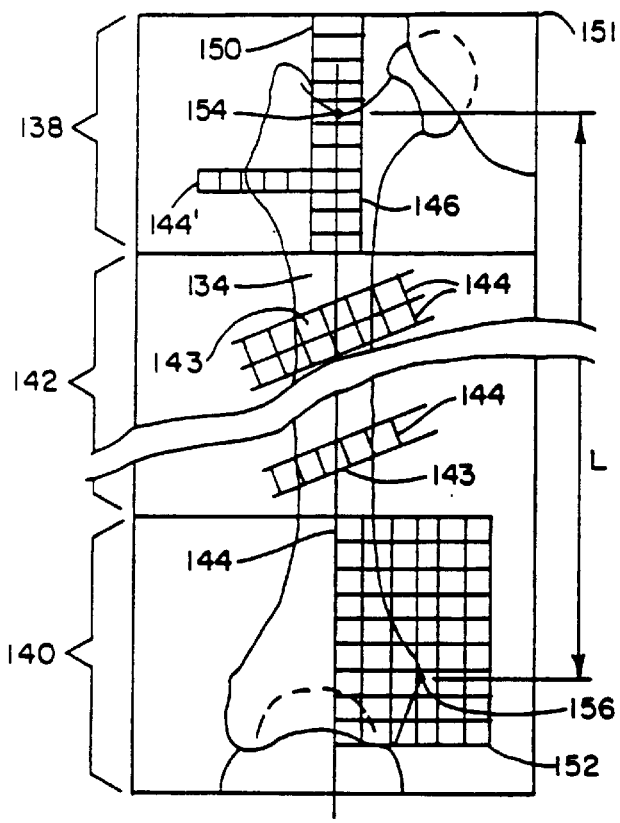
FIG. 12 is an illustration of an anterior-posterior view of a femur showing the determination of the femur's axis and the identification of fiducial points at the proximal and distal ends.
Figure 14:
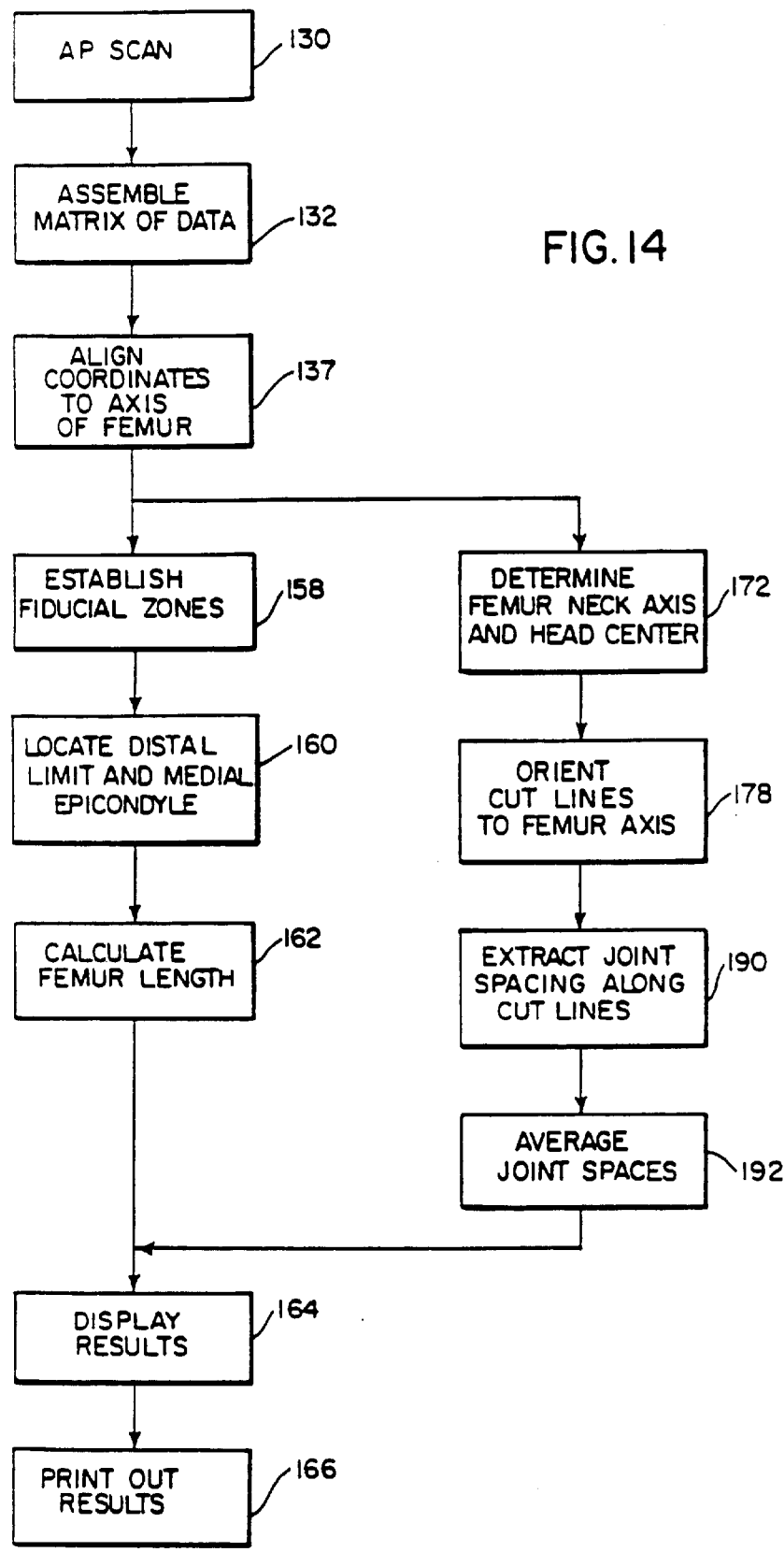
FIG. 14 is a flow chart similar to that of FIG. 5 showing the method of the present invention in measuring limb length and joint spacing.

Referring to FIGS. 12 and 14 in studying the human femur 134, it is preferred that the scan be taken from an anterior-posterior (AP) direction through the femur 134. The AP scan is indicated by process block 130. Once the scan has been completed, the data acquired in the scan is again assembled into a matrix of data values within the computer 18 as generally indicated by process block 132. Each data value within the matrix indicate the relative absorption of x-rays at each point of the scan. Thus the matrix provides both absorption data and location data.

As described above with respect to FIG. 3 after completion of the scan, the computer 18 automatically conducts a local comparison of data elements to determine the juncture of the data elements attributable to bone and data elements attributable to soft tissue. The threshold for the distinction between bone and soft tissue is determined by means of a graph as has been described.

Generally, the scanning direction 19 will not be perfectly aligned with the orientation of the femur 134. Instead, the angle between the long axis of the femur 134 and the scanning direction 19 will vary among patients 16 and even among different studies of the same patient 16.

Although this variation may be compensated for by a physician observing radiographs of the femur 134, differences between the orientation of the femur 134 and the scanning direction 19 can cause unacceptable variation in automated measurement of morphometric values.

Accordingly, the first step in the morphometric analysis of the femur 134 is a determination of the axis 146 of the femur as indicated generally by process block 137. The axis 146 substantially bisects the shaft of the femur 134 along its long axis and may serve as a reference for subsequent measurements. As will be understood, because the determination of the position of the axis 146 is determined by a large number of data values, the location of the axis 146 should be reproducible even in studies separated by considerable periods of time.

Determining the location of the axis 146 of the femur 134 requires that the matrix of data acquired be truncated by the operator, or according to automatic methods, to that data 151 contained within a rectangle roughly circumscribing the entire femur with a limited inclusion of other adjacent bones. Further, the femur axis 146 must be approximately oriented along the scanning direction 19. This selection and orientation is typically accomplished setting the limits and orientation of the AP scan per process block 130.

Once the relevant data is selected, a top portion 138 is identified including the superior one-sixth of the selected data 151 as measured along the scanning direction. Similarly, a bottom portion 140 including an inferior one-sixth of the selected data 151 is identified. The remaining central portion 142, including approximately two-thirds of selected data 151 generally excludes the ends (epiphysis) of the femur and include only the shaft (diaphysis).

In the central portion 142, each row 144 of data is analyzed and the center data value 143 of the bone values for that row 144 determined. The orientation of each row 144 (exaggerated in FIG. 12 for clarity) is perpendicular to the scanning direction 19 but generally not perpendicular to the long axis of the femur 134.

The process of identifying the centermost bone value for each data element in the rows 144 is repeated until a set of centers 143 are established along the long shaft of the femur 134. A line fit to these centers 143 establishes the femur axis 146. As noted above, the femur axis 146 provides a more reproducible reference for subsequent measurements than the scanning direction 19.

Once the femur axis 146 has been established, the data values of the matrix are rebinned as has been previously described so that the data values follow rows 144' and columns perpendicular and parallel to the axis of the femur 134.

Referring still to FIGS. 12 and 14, once the femur axis 146 has been located, two measurement zones 150 and 152 are established per process block 158 in order to identify fiducial points of the proximal limit 154 and the medial epicondyle 156. The former measurement zone 150 extends in a superior direction approximately from the beginning of the superior portion 138 (as determined from the rebinned data values) along the femur axis 146.

Within this measurement zone per process block 160, each rebinned row 144' is examined to find the superiormost row 144' still having bone values and aligned with the femur axis 146. This row is considered to be the height of the femur 134 and contains the proximal limit 154 and forms one endpoint for the measurement of the length of the femur 134.

The second measurement zone 152 extends in an inferior direction from the beginning of the inferior portion 140 and proximally from the femur axis 146. The position of the medial epicondyle 156 is considered to be the break in the smooth curve of the femur surface joining the diaphysis to the epiphysis. This break point may be determined by considering the first derivative of row value of the medialmost data element in each row 144 of the measurement region 152 identified to bone, as one progresses in an inferior direction. The first row 144' where the derivative goes to zero is considered the location of the medial epicondyle 156. This row 144' is taken as the second endpoint in the determination of the length of the femur 134.

Per process block 162, the femur length L may be calculated by subtracting the row coordinates for the two row endpoints embracing the proximal limit 154 and the medial epicondyle 156.

Once the femur length L has been calculated, the results may be displayed per process block 164 or printed out per process block 166 via the computer 18 and display 22. The length L may be displayed as a function of time, through the compilation of a number of measurements over a period of time or may be compared to a database of "normals" as previously described with respect to the vertebral measurements.

The length of the femur may be used to provide an indication of bone growth. Thus, it is of primary importance that measurements of femur length taken years apart may be accurately compared. The use of the fiducial points centered around the medial epicondyle and the proximal limit 154 is intended to provide such reproducibility. The referencing of the measurements to the femur axis 146 which is located by the mathematical combination of a large amount of data within region 142 helps ensure this reproducibility.

Figure 13:
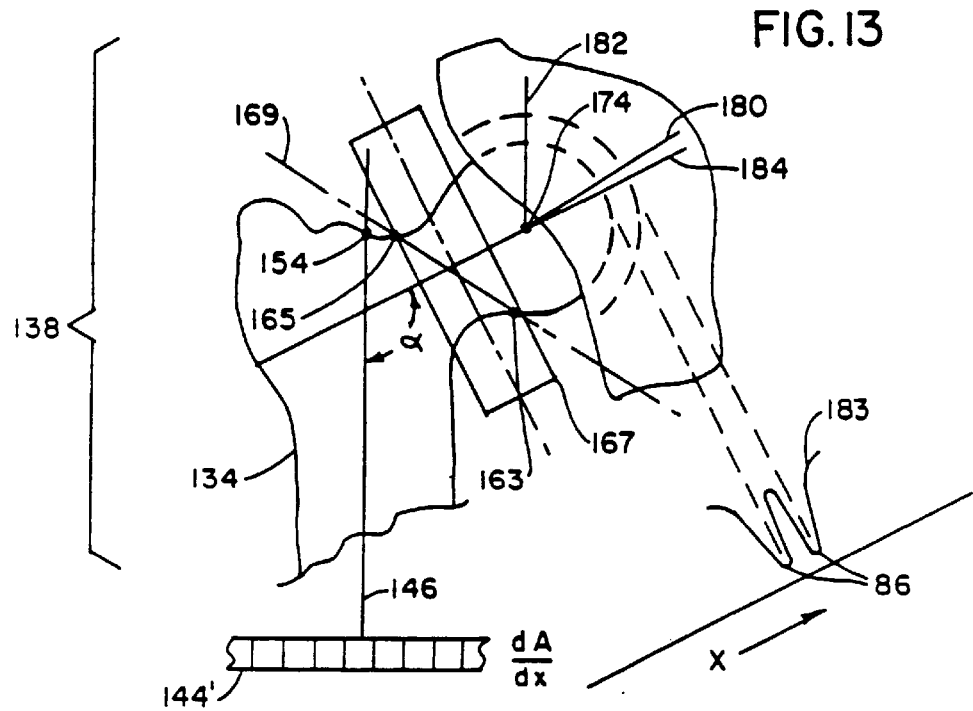
FIG. 13 is an anterior-posterior view of the interface between the femur head and the acetabulum showing the placement of cut lines to determine joint spacing as aligned with a graph showing rate of change in x-ray attenuation along one cut line used for the calculation of joint spacing.

Referring to FIGS. 13 and 14, a second measurement of the joint spacing between the femur head 170 and the acetabulum 168, may be performed on the femur 134. The measurement of joint spacing may permit the evaluation of joint function and the tracking of degenerative joint disease such as arthritis. Again, when measurements must be made over a period of time, it is imperative that variability caused by changes in the measurement technique rather than the joint spacing, be reduced to a minimum.

The joint spacing begins again with the determination of the femur axis 146, as has been previously described with respect to process blocks 130, 132, and 137, to provide a reproducible reference. Once the femur axis 146 has been identified, the data in the superior zone 138 and the medial side of the femur axis 146 is analyzed on a row by row basis, starting at the inferior edge of the superior zone 138 to identify an inferior and superior inflection point 163 and 165, respectively. The inferior inflection point 163 is the center of the last tissue data elements in a row 144' having bone values flanking them. Thus, inferior inflection point 163 is the highest point of the downward concavity of the femur neck. If two such points occur in a given row, the point closest to the femur axis 146 is selected.

The superior point of inflection 165 is the center of the first detected tissue elements having bone values flanking them after the inferior inflection point 163 as progressively superior rows of data 144' are examined. The superior point of inflection 165, then, is the lower most point of the upward concavity of the femur neck.

These points 163 and 165 are determined at process block 172 in preparation for determining a femur neck axis 184 of the femur neck and a center 174 of the femur head.

Once points 163 and 165 are determined, a measurement rectangle 167 having a width of one centimeter and a length of four centimeters is aligned with an inflection axis 169 passing through the points 165 and 163 such that the inflection axis 169 is coincident with the long axis of the measurement rectangle 167 and so that points 165 and 163 are equidistant from the center of the measurement rectangle 167.

Data elements within the measurement rectangle 167 are organized into rectangle rows along the rectangle's width and rectangle columns along the rectangle's length in a manner analogous to the rebinning described with respect to process block 137 and rows 144. The data elements of the measurement rectangle 167 are then analyzed to determine a centerline (not shown) across the width of the measurement rectangle 167 and symmetrically bisecting the bone elements contained within the measurement rectangle 167. Specifically, each rectangle column of data in the measurement rectangle 167 is analyzed to find the centermost data element within that rectangle column and a line is fit to those centerpoints. This centerline approximates the femur neck axis 184, that is, the line of symmetry of the extension of the femur's neck.

Once this centerline is determined, the measurement rectangle 167 is rotated so that its axis of symmetry along its width is aligned with this centerline. This realignment typically involves a translation and rotation of the measurement rectangle 167.

As rotated, the new data within the measurement rectangle 167 is arranged in new rows and columns with respect to the measurement rectangle and that data is analyzed to determine the rectangle column having the minimum length of contiguous bone elements among all rectangle columns within the measurement rectangle 167. This rectangle column corresponds roughly to the narrowest portion of the femur neck within the measurement rectangle 167. The measurement rectangle 167 is then moved along its short axis, and thus generally along the axis 184 of the femur neck, so as to position this determined minimum width of the neck approximately at the center rectangle column.

The determination of the centerline of the bone data within the rectangle columns of data is then repeated and the measurement rectangle shifted again to align its short axis with this centerline and the measurement rectangle is again moved to position the shortest column of bone data at its centermost column in an iterative fashion. These two steps of repositioning the measurement rectangle 167 are repeated until the incremental adjustments drop below a predetermined amount or for a predetermined number of times so that the measurement rectangle's short axis is coincident with the axis 184 of the femur neck and the measurement rectangle is positioned straddling the narrowest portion of the femur neck.

The position of the femur neck axis 184 is set equal to the short axis of the measurement rectangle 167, thus positioned.

For the purpose of measuring joint spacing and certain other dimensions, an average width of the femur neck is determined from the length of the bone elements in the centermost column of data of the measurement rectangle 167. Next, a centerpoint 174 corresponding approximately to the center of the femur head is identified along the femur neck axis 184 displaced from the center of the measurement rectangle 167 by the average neck width. This calculation reflects an approximation that the radius of the femur head is equal to the average width of the femur neck.

Minor variations in this location of the center point 174 may be tolerated because of the primary reliance on the location of the femoral axis 146.

At process block 178, cut lines 180 and 182 radiating from the center 174 are established based on a neck axis 184 and femur axis proceeding from the center 174. Cut line 182 is parallel to femur axis 146 proceeding in a proximal direction and cut line 180 is spaced from cut line 182 by 60° in a clockwise direction.

Between cut lines 180 and 182, five more cut lines are defined (not shown) proceeding from center point 174 and spaced at every 10° about that center point 174.

The values of the attenuation "A" of x-rays indicated by the data values of the matrix may be determined along each cut line by bilateral interpolation as is well understood in the art. The derivative 183 of these attenuation values (dA/dx) as a function of a distance x along the individual cut lines is then determined starting at the center point 174 and proceeding outward from the head 170 of the femur at process block 190.

The distance between the first two minima 186 of the derivative 183 along each cut line is taken as the joint spacing for that cut line and the joint spacings for all cut lines are averaged at process block 192 to produce an average joint spacing. The joint spacing may be displayed and printed out per process blocks 164 and 166 or may be compared to normals contained in a database of such values.

The ability to fix this measurement of joint spacing with respect to a robust reference of the femur axis 146 and to average a number of values of joint spacing improves the reproducibility of this measure.

Certain of the measurements obtained by these studies may be used for the purposes of evaluating the strength of the hip joint. For example, the angle between the femur axis 146 and the femur neck axis 184, together with the distance between the intersection of these two axes and the center 174 of the femur head, and the width of the femur neck provide a measure of the mechanical strength of the neck under the weight of the patient 16.

These measurements may also be performed on a patient 16 having an artificial hip joint so as to provide an indication of any possible shifting of the prosthetic joint with respect to the femur 136. This shifting may be characterized by changes in the distances between the center 174 and the intersection of the femur axis 146 and the femur neck axis 184, or the distance between this latter point and the intersection of the femur neck axis 184 with the lateral most portion of the femur 134.

Metacarpal Studies

Figure 15:
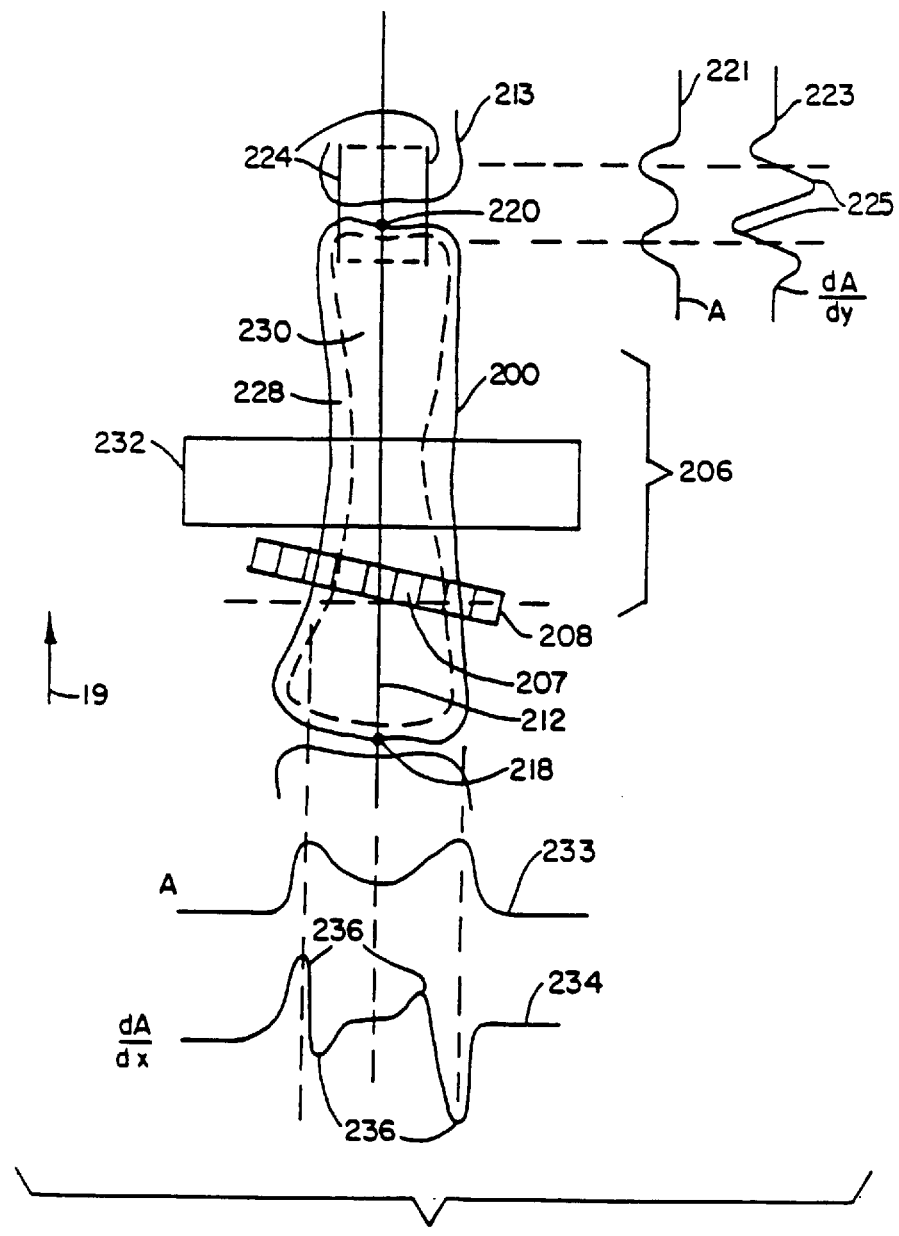
FIG. 15 is a planar view of a metacarpal bone of a human hand showing the determination of a reference axis with respect to measurements of cortical to trabecular bone and joint spacing within the hand.
Figure 16:
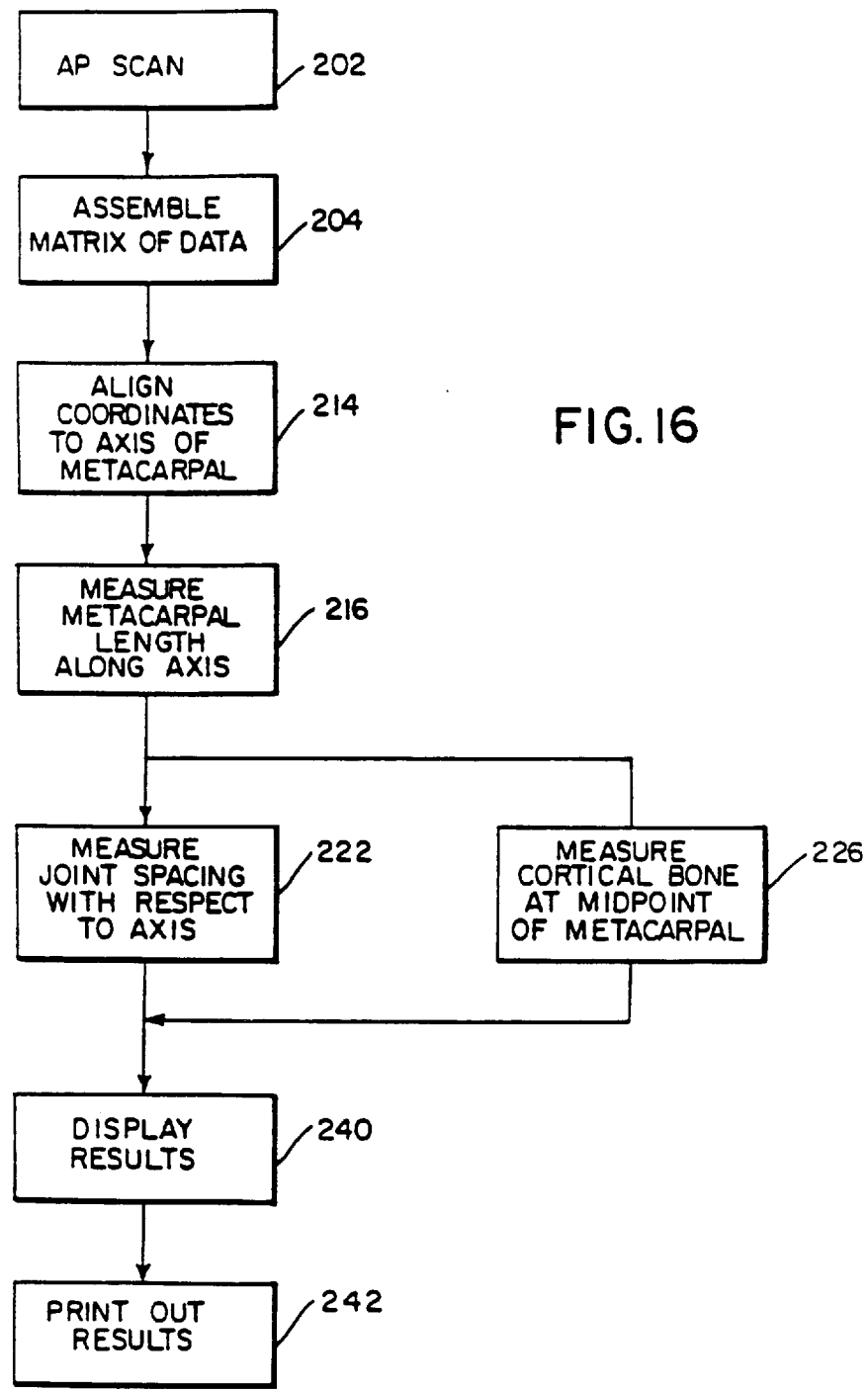
FIG. 16 is a flow chart similar to that of FIG. 14 showing the steps of obtaining the measurements shown in FIG. 15.

Referring now to FIGS. 15 and 16, similar studies to those described with respect to the femur 134 may be advantageously made of the human hand and in particular of the third metacarpal bone 200 (center finger) of the human hand.

Like the femur, it is preferred that the scan of the hand be taken in anterior/posterior direction with the hand in the anatomic position, that is, from the back of the hand through the palm of the hand, per process block 202. Again, the scan data is assembled into a matrix of data values within computer 18 as generally indicated by process block 204.

The third metacarpal bone 200 to be measured is generally identified by the operator by selecting a point on the metacarpal bone 200 and selecting that data related to the third metacarpal by connectivity algorithms known in the art. Alternatively, this selection process may be performed automatically.

Generally, the hand of the patient 16 is oriented so that the metacarpal bone 200 extends along the columns of scan data indicated by scanning direction 19. However, it will be understood as described above that the columns of scan data will not necessarily align with the axis of the metacarpal bone 200. For this reason in a manner analogous to those described above, coordinates are first established with respect to the metacarpal bone 200.

In particular, once the data elements have been isolated into bone or soft tissue and according to those associated with the metacarpal bone 200, a center portion 206 of the data of the metacarpal bone 200 covering the diaphysis is selected and the centermost bone value 207 of each row 208 within this center portion 206 is identified and aligned to fit to those centers 207 indicating the metacarpal axis 212. As with the femur, the center portion of the data used for the determination of the metacarpal axis 212 may be the center two thirds of the rows of the scan matrix.

Once this metacarpal axis 212 is determined, the data values are rebinned as has been described so that subsequent measurements may be made with respect to this axis 212. This rebinning is indicated at process block 214.

The metacarpal length is readily determined, per process block 216, by reviewing the rebinned data along the column aligned with metacarpal axis 212. A distal point 220 is determined by moving distally from the center region of the metacarpal bone 200 along the metacarpal axis 212 until the first non-bone value is detected, that non-bone value corresponding to cartilage between the metacarpal and the proximal phalanx 213. Likewise, a proximal point 218 is determined by moving proximally from the center region of the metacarpal bone 200 along the metacarpal axis 212 until the first non-bone value is detected.

Joint spacing between the distal epiphysis of the metacarpal bone 200 and the opposing face of the proximal phalanx 213 may next be determined, as indicated by process block 222, by evaluating the rebinned data symmetrically located on either side of the metacarpal axis 212 within a predetermined range indicated by lines 224 and proceeding distally until the first bone values are detected in each column of rebinned data after the end of bone values of the metacarpal bone 200. The total area of non-bone data contained between the bones of the metacarpal bone 200 and the proximal phalanx 213 is then divided by the number of columns within the range of lines 224 to provide a joint spacing having the robustness of a statistical average.

Alternatively, each column of data 221 near the joint and within the range indicated by lines 224 may be differentiated to produce a derivative graph 223. The positive and negative peaks 225 about the nonbone values of the joint cartilage are taken as the opposed ends of the distal epiphysis and the metacarpal bone 200 and their separation measured. The average separation for each column of data 221 within lines 224 is then averaged to produce a value of joint spacing.

Yet another measurement that may be advantageously made once the data has been rebinned is that of cortical thickness as indicated by process block 226. Within the data of the metacarpal bone 200, as isolated from soft tissue by the graph process previously described, is a denser cortical layer 228 and a less dense trabecular center 230. The relative proportions of these two portions 223 and 230 may provide a more sensitive measure of the change in bone structure than, for example, the thickness of the metacarpal bone 200. This measurement involves differentiating between these two different bone types within the data acquired.

The first step in such measurements is to position the measurement rectangle 232 at the center of the metacarpal bone 200. This may be done automatically as guided by the previous measurements of axis 217 and points 220 and 218. The measurement rectangle 232 has a width, oriented along the axis of the metacarpal bone 200, of 0.5 cm and a length of 2.0 cm. The exact size of the measurement rectangle 232 may be adjusted depending on the patient's size as will be apparent to those of ordinary skill in the art. Each row of data values 233 within the measurement rectangle 232, aligned across the metacarpal axis 212, is differentiated to produce a derivative graph 234. The positive and negative peaks 236 of this graph 234 are taken as the locations of the interfaces between soft tissue and cortical bone and between cortical bone and trabecular bone. These locations are averaged with others of its kind for each row of the data of the measurement rectangle 232 to provide average measurements of cortical and trabecular thickness for the indicated 0.5 cm. of length.

The results of process blocks 216, 222, and 226 may be displayed and printed out for review per process blocks 240 and 242. The values may be reviewed directly or compared to statistical norms contained within a data base of standard values.

Detection of Crush Fractures

Figure 19:
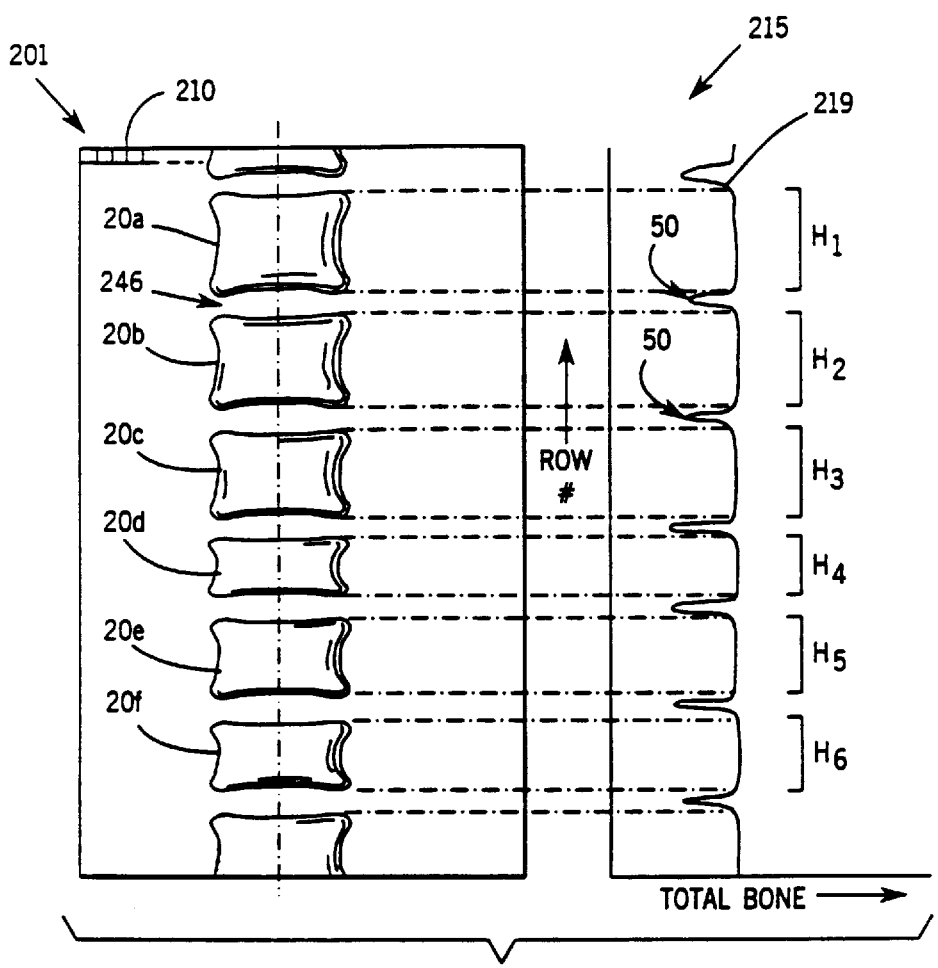
FIG. 19 is a schematic representation of an anterior-posterior scan of a spine showing regions of pixels measuring bone and a graph aligned with the scan having a vertical axis corresponding to vertical location in the scan and a horizontal axis corresponding to the sum of pixel values for a row of scan data permitting the identification of the vertebra by minimas or rows of low total bone value.

Referring now to FIG. 19, a matrix of data 201 having horizontal rows and vertical columns of pixels 210 may be obtained by an anterior-posterior scan of the patient as described previously with respect to FIG. 5, process blocks 60 and 62. Each pixel 210 may be identified to either bone or soft tissue as also previously described and as is generally known in the art. Preferably, the matrix 201 covers a number of vertebrae 20(a) through 20(f).

From the scanned matrix 201, the computer 18 may determine values for a graph 215 much like that of FIG. 4, plotting the total bone content of the pixels 210 in each row of the matrix 201 against row number, to produce a total bone graph line 219. This graph line 219 will have periodic minima 50 for rows of pixels 210 that extend through the intervertebral spaces 246 of the spine. These minima 50 may be used to identify each of the pixels 210 to particular vertebrae 20(a) through 20(f). That is, pixels 210 in a row above the row of a minima 50 and below the row of the next higher minima 50 are identified to the same vertebra 20.

For each such vertebrae 20(a) through 20(f), a height $H_1$–$H_6$ may now be determined directly from graph 219 either by measuring the separation between the minima 50, already calculated, or preferably by taking the first row of graph line 219 having a total bone value exceeding a predetermined threshold, for example 30% of the peak value of the graph 219 between the minimas 50, for a particular vertebra 20.

Generally, there will be some variation between the values of $H_1$–$H_6$ for a given healthy individual but substantially more variation between particular values of $H_1$–$H_6$ between healthy individuals.

Figure 20:
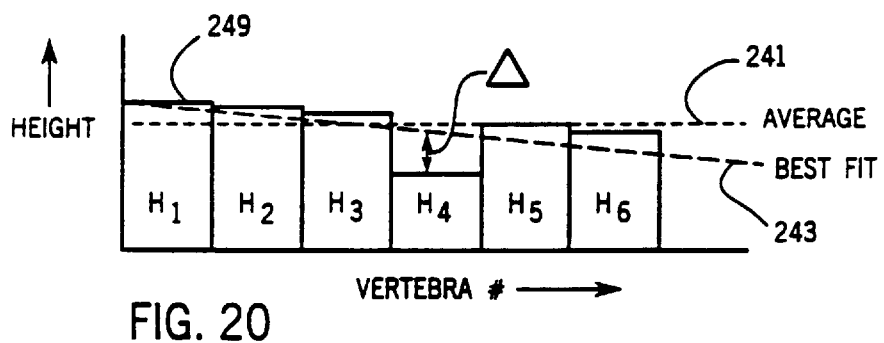
FIG. 20 is a graph of height of each vertebra, as determined from FIG. 19, by order of vertebra in the spine showing the determination of a typical vertebral height by two methods which provide a standard against which to detect crush fractures of the vertebrae.

Referring now to FIG. 20, the height values $H_1$–$H_6$ may be effectively plotted by the computer 18 against the order of their respective vertebrae 20(a) through 20(f) or according to the vertical center of the vertebra 20(a) through 20(f) as computed from the values $H_1$–$H_6$, but in either case preserving the sequence of those vertebrae 20 to produce bar chart 248. A simple arithmetic average 241 of the values $H_1$–$H_6$ may be computed and this average compared to each value $H_1$–$H_6$ to produce a deviation value D as follows:

$$D = H_i - \frac{1}{N} \sum_{k=1}^{N} H_k. \tag{1}$$

where N is the total number of vertebra measured. Here, large negative deviations D indicate a possible crush fracture of the corresponding vertebra 20 which may suggest discounting the validity of the density measurement obtained from that vertebra 20.

In the example of FIGS. 19 and 20, both the vertebra 20(f) ($H_6$) and 20(d) ($H_4$) are somewhat smaller than the average 241. However, vertebra 20(d) is significantly smaller leading to an indication of possible crush fracture. The amount of deviation that indicates a crush fracture is a clinical determination that must be developed empirically.

Alternatively, the normal variation in heights $H_1$–$H_6$ of vertebra 20 as one moves through the spine of an individual may be accommodated by fitting a line or curve of low order 243 to the height values $H_1$–$H_6$. In the example of FIGS. 19 and 20, the vertebral height H decreases somewhat from top to bottom. Here, a straight line fit, using well known techniques such as least squares, produces a statistical measure exceeded by all the vertebra 20 except vertebrae 20(d) which as previously described may have a crush fracture.

Alternatively, the height values $H_1$–$H_6$ may be compared to a database of normal values, where again the normals are adjusted for body height, sex, and weight of the individual patient, as well as for maturity of the individual. The normals may be further adjusted based on the statistical measure of the vertebrae of the individual, again making the assumption that the majority of the vertebrae are healthy.

Thus, the technique provides a threshold for determining that a vertebra is fractured that is automatically tailored to the individual, and that can be tailored even to variations of vertebrae within the individual. This technique potentially eliminates the need for a routine lateral scan of the patient, but nevertheless provides an indication that lateral scans may be desirable to detect other indicia of fractures such as concavity and wedge angles. Generally, the invention makes a robust bone density measurement possible with a single anterior posterior scan.

Side by Side Detector

Figure 21:
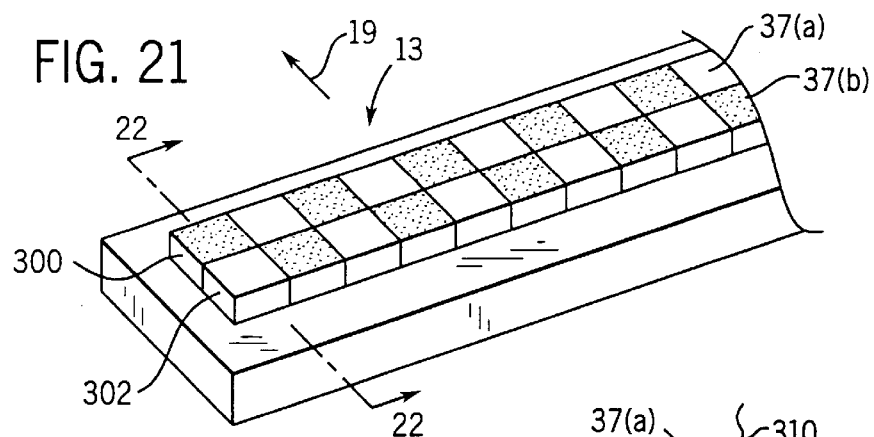
FIG. 21 is a perspective view of the detector of FIG. 18(a) having two rows of high and low energy detector elements arranged in a "checkerboard" pattern according to one embodiment of the present invention.

Referring to FIG. 21, the detector 13 may support on a face exposed to x-rays, a number of high energy detector elements 37(a) and low energy detector elements 37(b) arranged in two rows 300 and 302 extending in a direction generally perpendicular to the scanning direction 19.

Within each row 300 and 302, the high energy detectors 37(a) alternate with the low energy detectors 37(b). Further, high energy detectors 37(a) alternate with low energy detectors 37(b) along columns perpendicular to the rows and aligned with the scanning direction 19. Thus the detectors are laid out in a "checkerboard" fashion within the two rows.

Figure 23:
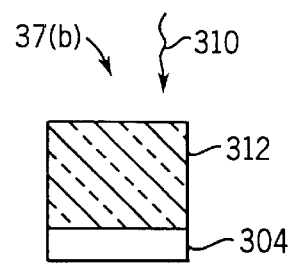
FIG. 23 is a cross-sectional view along line 22—22 of a high energy detector element.

Referring now to FIG. 23, the low energy detector 37(b) includes a photodiode 304 coated on its surface facing oncoming x-rays 310 with a scintillation material 308. X-rays 310 passing through the scintillation material 308 produce light which may be detected by the photodiode 304. The photodiode 304 provides an electrical signal in response to the light which may be processed to produce an intensity signal as is understood in the art.

Figure 22:
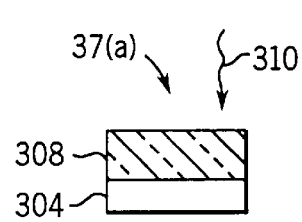
FIG. 22 is a cross-section along line 22—22 of FIG. 21 through a low energy detector element.

Referring now to FIG. 22, the high energy detector 37(b) is similarly constructed including a photo diode 304 and a scintillating material 312 providing good sensitivity to high energy x-rays. The high energy detector element 37(b) is capped by a filter 314 to block low energy x-rays prior to their reaching the scintillator 312. In between the scintillation material 308 and the diode 304 is a layer of lead impregnated glass 306 to block radiation 310 not absorbed by the scintillation material 308 yet to pass light from the scintillator 312.

The scintillation materials 308 and 312 are selected according to the desired energy sensitivity of the detector element according to methods known in the art. Detector element arrays of this type are commercially available from a number of sources including Thomson Dube Electroniques of France.

Figure 24:
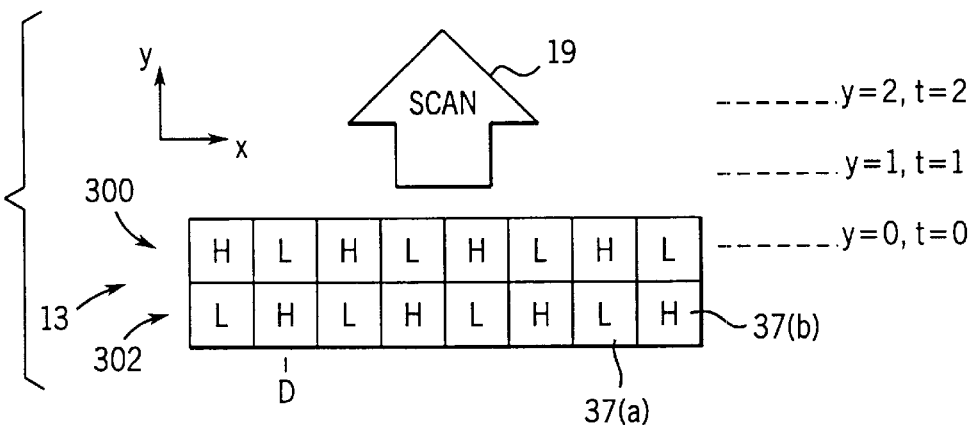
FIG. 24 is a schematic plan view of the detector of FIG. 21 showing a direction of scanning and its location at different times.

Referring now to FIG. 24, the detector 13 is scanned across an imaged object in a scanning direction 19 to receive x-rays passing though the imaged object and to measure their attenuation. It will be understood that the scanning motion need only be relative to the imaged object and may or may not involve movement of the detector 13.

Electrical signals from each of the detector elements 37(a) and 37(b) are sampled during this scanning so as to provide data over the swept area of the detector array 13. The sampling is timed so that a sample is obtained at times t=0, t=1, t=2, etc. and at locations y=0, y=1, y=2, etc. where the difference between y locations is equal to the width of a detector element 37(a) or 37(b) measured along the scanning direction 19.

Thus, as a result of their being two rows 300 and 302, each volume element of the imaged object is measured sequentially by two detector elements, a low energy detector element 37(a) and a high energy detector element 37(b), not necessarily in that order.

These two sequential measurements could be combined for the purpose of making a dual energy analysis of that volume element of the imaged object, however, because the two measurements are made at different times, any motion of the imaged object would produce errors in the resulting quantitative measurement.

Figure 25:
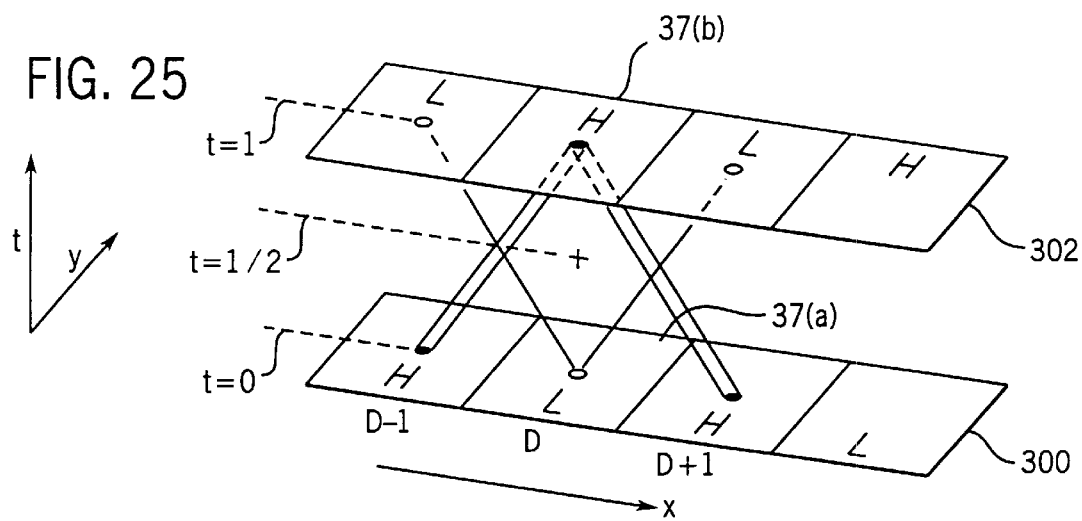
FIG. 25 is a graph depicting the detector elements of the detector of FIG. 24 at two times and locations showing the interpolation of data from the different detector elements to a common time and location for both high and low energy elements.

Referring now to FIGS. 24 and 25 in the present invention, the measurements are instead combined to reduce motion artifacts and edge artifacts. As depicted in FIG. 25, each x and y location (with respect to the imaged object) is measured twice, first by a detector element in row 300 and then by a detector element in the same column but in row 302. At time t=0, a given x-axis location of the patient designated x=D, y=0 will be measured by a low energy detector element 37(a). Whereas at time t=1, the same location on the imaged object (x=D, y=0) will be measured by a high energy detector 37(b).

Because of the alternating arrangement of high and low energy detectors 37(a) and 37(b), at t=0, y=0, high energy measurements will also be made for x locations D−1 and D+1. Similarly, at t=1, y=0, low energy measurements will be made at x locations D−1 and D+1.

These multiple measurements permit a three-point interpolation to be made to provide a virtual high energy measurement and virtual low energy measurement to be computed for location x=D, y=0 at a common time t=½. In particular, the virtual high energy measurement $H_{1/2,0}$ is:

$$H_{1/2,0} = H_{1,D} + \tfrac{1}{2}(H_{0,D-1} + H_{0,D+1}) \qquad (1)$$

and the low energy measurement is:

$$L_{1/2,0} = L_{0,D} + \tfrac{1}{2}(L_{1,D-1} + L_{1,D+1}) \qquad (2)$$

where L and H represent the measurements from low and high energy detector elements respectively, the first subscripts indicating the time of the measurement (or virtual time) and the second subscript indicating the x-axis location of the detector element within a row.

As can be seen in the present invention, measurements are combined that have different times and locations. The symmetry of the detector array 13 allows a common interpolation factor to be used in interpolating both between times and locations which could not be done with other configurations.

It should be noted that an interpolation could be done within a single row, for example 302, by averaging the values of $L_{D-1}$ and $L_{D+1}$ to produce a virtual measurement at location $L_D$ which could be combined with the measurements made by detector $H_D$ in that same row. In this case, only interpolation over a space is performed, not over time. However, because no low energy measurement is made exactly at the location of the high energy detector $H_D$, the measurement is susceptible to edge artifacts. For example, where detector $L_{D-1}$ of row 302 receives a substantially greater value of x-ray flux than the high energy detector $H_D$ of row 302, the interpolation of a low energy measurement to the location of $H_D$ will be unduly high.

Figure 26:
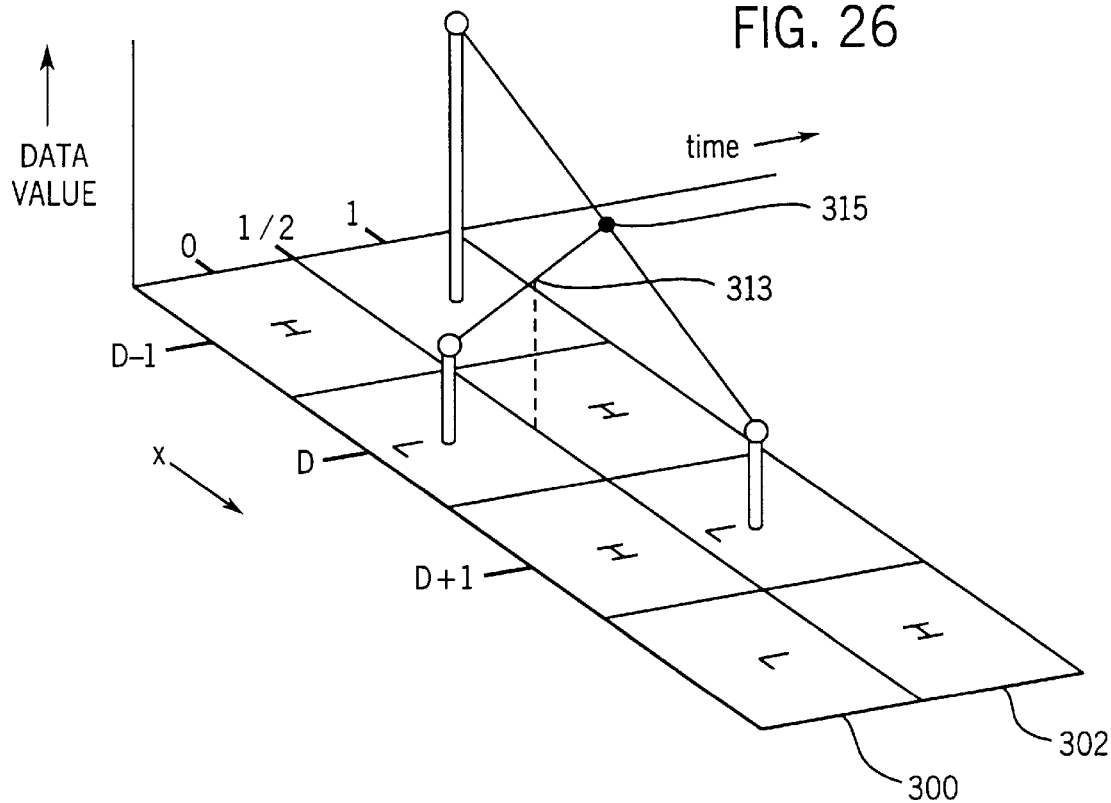
FIG. 26 is a graph depicting example values from low energy detector elements showing how the interpolation among three detector elements reduces edge effects caused by extreme attenuations off center from the point of measurement.

Referring now to FIG. 26, a different representation of the measurements of equation (2) is shown in which the values of the data are indicated by vertical bars. A three point interpolation minimizes the edge artifacts. In the case described above, the detector measurement $L_{1,D-1}$ shows a disproportionately high x-ray fluence compared to, for example, the detector $L_{0,D}$. The three point interpolation provided above yields a value of $L_{1/2,D}$ at point 313 that is significantly lower (a presumably more accurate) than the simple two point interpolation of a value of $L_{1,D}$ indicated at point 314. The two point interpolation does not include a measurement taken directly at the x-axis location of the desired data.

Figure 27:
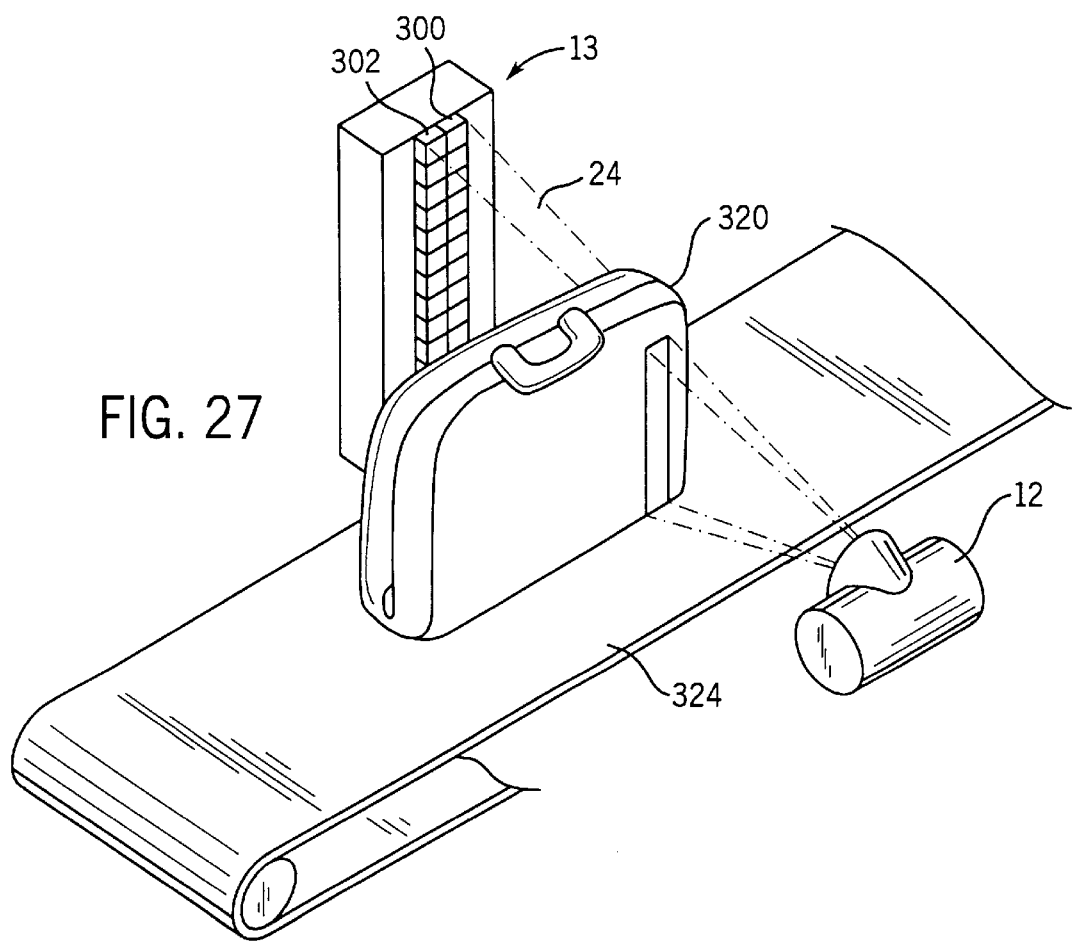
FIG. 27 shows a perspective view of the present invention used in a baggage scanning application.

Referring now to FIG. 27, the high efficiency and high resolution of the above described side-by-side detector is suitable not only for medical imaging but for other imaging application such as the imaging of baggage 320. Here the ability to distinguish between materials within the bag, as is provided by dual energy techniques, is important but high resolution and resistance to motion artifacts caused by movement of the materials in the bag as it is transported, must also be considered.

In this application, the detector 13 may place the two rows 300 and 302 in vertical configuration to receive a fan beam 23 of x-rays passing through baggage 320 from x-ray source 12. Conveniently, bag 320 may be moved on a conveyor belt 324 to provide the desired scanning motion.

It is thus envisioned that the present invention is subject to many modifications which will become apparent to those of ordinary skill in the art. Accordingly, it is intended that the present invention not be limited to the particular embodiment illustrated herein, but embraces all such modified forms thereof as come within the scope of the following claims.

We claim:

1. A dual energy x-ray detector comprising:

low energy solid state x-ray detector elements detecting incident low energy x-ray photons each over a predetermined detector area to produce a first electronic signal proportional to the incident low energy photons; and high energy solid state x-ray detector elements detecting incident high energy x-ray photons each over a predetermined detector area to produce a second electronic signal proportional to the incident high energy photons;

wherein the low and high energy x-ray detector elements are arranged in at least one row of alternating high and low energy detector elements.

2. The dual energy detector of claim 1 including in addition a detector scanning assembly moving the detector with respect to an imaged object in a direction perpendicular to the row.

3. The dual energy detector of claim 1 including at least two rows and wherein the low and high energy detector elements are also arranged in columns of alternating high and low energy detector elements perpendicular to the rows.

4. The dual energy detector of claim 1 wherein the high and low energy detecting elements each include an x-ray sensitive scintillator and a photodiode.

5. A dual energy x-ray detector comprising:

low energy detector elements detecting incident low energy x-ray photons each over a predetermined detector area; and high energy detector elements detecting incident high energy x-ray photons each over a predetermined detector area;

wherein the low and high energy detector elements are arranged in at least one row of alternating high and low energy detector elements including an interpolation circuit receiving electrical signals from at least two high energy detecting elements and combining these electrical signals to produce an interpolated value for a virtual high energy detecting element located at the same location as a measurement of low energy.

6. The dual energy detector of claim 5 wherein the interpolation circuit is an electronic computer.

7. A solid state dual energy x-ray detector comprising:

low energy detector elements detecting incident low energy x-ray photons each over a predetermined detector area; and high energy detector elements detecting incident high energy x-ray photons each over a predetermined detector area;

wherein the low and high energy detector elements are arranged in at least one row of alternating high and low energy detector elements including an interpolation circuit receiving electrical signals from at least two low energy detecting elements and combining these electrical signals to produce an interpolated value for a virtual low energy detecting element located at the same location as a measurement of high energy.

8. The dual energy detector of claim 7 wherein the interpolation circuit is an electronic computer.

9. A dual energy x-ray detector comprising:

low energy detector elements detecting incident low energy x-ray photons each over a predetermined detector area; and high energy detector elements detecting incident high energy x-ray photons each over a predetermined detector area;

wherein the low and high energy detector elements are arranged in at least one row of alternating high and low energy detector elements including an interpolation circuit receiving at a first and second time, electrical signals from at least two detecting elements and combining these electrical signals to produce an interpolated value for a virtual detecting element taken at a third time.

10. The dual energy detector of claim 9 wherein the third time is halfway between first and second times.

11. A method of acquiring dual energy incidence data with a dual energy detector having low energy detector elements detecting incident low energy photons each over a predetermined detector area, high energy detector elements detecting incident high energy photons each over a predetermined detector area wherein the low and high energy detector elements are arranged in at least one row of alternating high and low energy detector elements, the method comprising the steps of:

(a) at a first time, acquiring data at a first location with respect to an imaged object from the high and low energy detectors of a first row;

(b) moving the rows of detector elements generally perpendicular to the extension of the row with respect to the imaged object;

(c) at a second time, acquiring data at the first position from the high and low energy detectors of a second row; and (d) interpolating the data acquired at the first and second time to a common interpolated time and location.

12. The method of claim 11 wherein the moving of step (b) moves the rows of detectors by the width of a detector element measured perpendicularly to the extension of the row.

13. The method of claim 11 wherein the common interpolated time is halfway between the first and second times.

14. The method of claim 11 wherein the common interpolated location is centered on a detector element.

15. A bone densitometer comprising:

(a) an x-ray source producing a beam of x-ray radiation;

(b) a patient support positioning a patient within the poly-energetic beam;

(c) a dual energy detector receiving the beam after it has passed through the patient to generate electrical signals indicating the attenuation of the beam by the patient within distinct first and second energy ranges, the dual energy detector including:
  (i) low energy detector elements detecting incident low energy photons each over a predetermined detector area;
  (ii) high energy detector elements detecting incident high energy photons each over a predetermined detector area; wherein the low and high energy detector elements are arranged in at least one row of alternating high and low energy detector elements; and
(d) an electronic computer receiving and combining the electrical signals to produce a bone density image based on the attenuation of the x-ray radiation in the first and second ranges;
wherein the computer combines the electrical signals from at least two high energy detecting elements to produce an interpolated value for a virtual high energy detecting element located at the same location as a measurement of low energy.

16. A baggage scanning system comprising:
(a) an x-ray source producing a beam of x-ray radiation;
(b) a bag conveyor moving the bag across the beam;
(c) a dual energy detector receiving the beam after it has passed through the patient to generate electrical signals indicating the attenuation of the beam by the patient within distinct first and second energy ranges, the dual energy detector including:
  (i) low energy detector elements detecting incident low energy photons each over a predetermined detector area;
  (ii) high energy detector elements detecting incident high energy photons each over a predetermined detector area;
wherein the low and high energy detector elements are arranged in at least one row of alternating high and low energy detector elements; and
(c) an electronic computer receiving and combining the electrical signals to produce a material differentiating image based on the attenuation of the x-ray radiation in the first and second energy ranges;
wherein the computer combines the electrical signals from at least two high energy detecting elements to produce an interpolated value for a virtual high energy detecting element located at the same location as a measurement of low energy.

* * * * *